(12) United States Patent
Davalian et al.

(10) Patent No.: US 6,190,873 B1
(45) Date of Patent: Feb. 20, 2001

(54) CYCLOSPORIN ASSAY AND KIT

(75) Inventors: Dariush Davalian, San Jose; Maureen H. Beresini, Moss Beach; Svetlana Alexander, Sunnyvale; Mae Wan-Leng Hu, Los Altos Hills; Edwin F. Ullman, Atherton, all of CA (US)

(73) Assignee: Dade Behring Marburg GmbH, Marburg (DE)

( * ) Notice: Under 35 U.S.C. 154(b), the term of this patent shall be extended for 0 days.

(21) Appl. No.: 08/402,296

(22) Filed: Mar. 10, 1995

Related U.S. Application Data

(62) Division of application No. 08/044,561, filed on Apr. 7, 1993, now abandoned, which is a continuation of application No. 07/616,116, filed on Nov. 20, 1990, now abandoned.

(51) Int. Cl.[7] ....................... G01N 33/535; G01N 33/545

(52) U.S. Cl. .................. 435/7.93; 435/188; 435/962; 436/518; 436/531; 436/536; 436/545; 436/546; 436/815; 436/825; 530/389.8; 530/405

(58) Field of Search ................................. 435/7.93, 962; 436/815, 518, 531, 536, 545, 546, 825

(56) References Cited

U.S. PATENT DOCUMENTS

| | | |
|---|---|---|
| 4,117,118 | 9/1978 | Harri et al. . |
| 4,384,996 | 5/1983 | Bollinger et al. . |
| 4,396,542 | 8/1983 | Wenger . |
| 4,639,434 | 1/1987 | Wenger et al. . |
| 4,727,035 | 2/1988 | Mahoney . |
| 4,764,503 | 8/1988 | Wenger . |
| 5,089,390 | 2/1992 | Davalian et al. . |
| 5,169,773 | 12/1992 | Rosenthaler, et al. . |
| 5,350,574 | * 9/1994 | Erlanger et al. ..................... 530/405 |
| 5,405,785 | * 4/1995 | Erlanger et al. ..................... 436/531 |

FOREIGN PATENT DOCUMENTS

| | | |
|---|---|---|
| 0 044 441 A1 | 1/1982 | (EP) . |
| 0 283 801 A2 | 9/1988 | (EP) . |
| WO 86 02080 | 4/1986 | (WO) . |

OTHER PUBLICATIONS

B. Erlanger, Methods in Enzymology vol. 70, pp. 85–104 (1980).*
M. Brinkley, Bioconjugate Chem., vol. 3, pp. 2–13 (1992).*
I. Maggio, Enzyme–immunoassay, Chemical Aspects of Enzyme–immunoassay (Chapter 4), CRC Press, Inc. (1980).*
V. Quesniaux et al., Prog. Allergy, vol. 38, pp. 108–122, 1996.*
B. Ryffel et al., Transplantation Proceedings, vol. XX, No. 2, Suppl. 2 (Apr.), 1988 pp. 575–584.*
Ball, et al., Clinical Chemistry, vol. 34:2, (1988) pp. 257–260, "Specific $^3$H Radioimmunoassay with a Monoclonal Antibody for Monitoring Cyclosporine in Blood".
Bowers, et al., Transplantation Proceedings, vol. XVIII, No. 6, Suppl 5, (Dec. 1986) pp. 137–143, "Studies of Cyclosporine Blood Levels: Analysis, Clinical Utility, Pharmacokinetics, Metabolites, and Chronopharmacology".
Cacalano, et al., J. Immunological Methods, vol. 118, (1989) pp. 257–263, "Antibodies to cyclosporine A (CsA) by a novel route and their use to monitor cyclosporine levels by radioimmunoassay".
Christians, et al., Clinical Chemistry, vol. 34:1, (1988) pp. 34–39, "Liquid–Chromatographic Measurement of Cyclosporin A and Its Metabolites in Blood, Bile, and Urine".
Donatsch, et al., J. Immunoassay, vol. 2:1, (1981) pp. 19–32, "A radioimmunoassay to measure cyclosporin A in plasma and serum samples".
Hawk's Cay Meeting Transplanation Proceedings, vol. 22:3, (1990) pp. 1357–1361, "Consensus Document: Hawk's Cay Meeting on Therapeutic Drug Monitoring of Cyclosporine".
Maurer, et al., Drug Metabolism and Disposition, vol 12:1, (1984) pp. 120–126, "Disposition of cyclosporine in several animal species and man".
McBride, et al., Clinical Chemistry, vol. 35:8, (1989) pp. 1726–1730, "Measurement of Cyclosporine in Plasma from Patients with Various Transplants: HPLC and Radioimmunoassay with a Specific Monoclonal Antibody Compared".
Quesniaux, et al., Immunology Letters, vol. 9, (1985) pp. 99–104, "An enzyme immunoassay for the screening of monoclonal antibodies to cycloporin".
Quesniaux, et al., Molecular Immunology, vol. 24:11 (1987) pp. 1159–1168, "Fine specificity and cross–reactivity of monoclonal antibodies to cyclosporine".

(List continued on next page.)

*Primary Examiner*—Mary E. Ceperley

(57) ABSTRACT

A method of measuring the amount of cyclosporin in a sample suspected of containing cyclosporin is disclosed. A method of inactivating interfering cross-reactive material in an assay for measuring the amount of cyclosporin in a sample suspected of containing cyclosporin is also disclosed. Compositions wherein cyclosporin is conjugated to an immunogenic carrier or a label, optionally through a linking group, at an alanine nitrogen atom of the cyclic backbone of cyclosporin are also disclosed. Compositions wherein atiocyclosporin is conjugated, optionally through a linking group, to an immunogenic carrier or a label are also disclosed. Where cyclosporin is conjugated to an immunogenic carrier, the conjugates may be used as immunogens for the preparation of antibodies which are capable of recognizing cyclosporin. Where atiocyclosporin is conjugated to an immunogenic carrier, the conjugates may be used as immunogens for the preparation of antibodies which are capable of recognizing interfering cross-reactive material but substantially incapable of recognizing cyclosporin or cyclosporin-label conjugates. Where cyclosporin is conjugated to a label, the conjugates may be used as part of a signal producing system in cyclosporin assays. Both the antibodies and label conjugates are useful in the disclosed assay methods.

57 Claims, No Drawings

OTHER PUBLICATIONS

Quesniaux, et al., Clinical Chemistry, vol. 33:1, (1987) pp. 32–37 "Potential of Monoclonal Antibodies to Improve Therapeutic Monitoring of Cyclosporine".

Rosano, et al., Transplanation Proceedings, vol. XVIII, No. 6, Suppl 5, (Dec. 1986) pp. 35–40 "Cyclosporine Metabolites in Human Blood and Renal Tissue".

Sandoz Ltd., Ciclosporin RIA–Kit, Instructions for Use, 2nd Edition (Jun. 1983) pp. 1–21.

Sanghvi, et al., Clinical Chemistry, vol. 34:9, (1988) pp. 1904–1906 "Abbott's Fluorescence Polarization Immunoassay for Cyclosporine and Metabolites Compared with the Sandoz "Sandimmune" RIA".

Traber, et al., The Journal of Antibiotics, vol. XLII, No. 4, (Sep. 19, 1988), pp. 591–597, "Cyclosporins—New Analogues by Precursor Directed Biosynthesis".

Schran, et al., Clinical Chemistry, vol. 33:12, (1987) pp. 2225–2229, "Determination of Cyclosporine Concentrations with Monoclonal Antibodies".

Vernillet, et al., Clinical Chemistry, vol. 35:4, (1989) pp. 608–611, "Determination of Cyclosporine in Plasma: Specific Radioimmunoassay with a Monoclonal Antibody and Liquid Chromatography Compared".

Wolf, et al., Clinical Chemistry, vol. 34:1 (1989) pp. 120–124 "Measurement of Cyclosporine Concentrations in Whole Blood: HPLC and Radioimmunoassay with a Specific Monoclonal Antibody and $^3$H–or $^{125}$I–Labeled Ligand Compared".

* cited by examiner

CYCLOSPORIN ASSAY AND KIT

CROSS-REFERENCE TO RELATED APPLICATIONS

This application is a division of application Ser. No. 08/044,561, filed Apr. 7, 1993, now abandoned, which is a continuation of application Ser. No. 07/616,116, filed Nov. 20, 1990, now abandoned.

BACKGROUND OF THE INVENTION

1. Field of the Invention

The body relies upon a complex immune response system to distinguish self from non-self. The proper functioning of the immune system is vital for the long term health of the body.

Deficient immune response can lead to the body's inability to protect itself from non-self matter. Excessive immune response can lead to the body's over reaction to what would otherwise be innocuous matter.

At times, the body's immune system must be controlled in order to either augment a deficient response or suppress an excessive response. For example, when organs such as kidney, heart, heart-lung, bone marrow, and liver are transplanted in humans, the body will sometimes reject the transplanted tissue by a process referred to as allograft rejection.

In treating allograft rejection, the immune system is frequently suppressed in a controlled manner through drug therapy. Immunosuppressant drugs are carefully administered to transplant recipients in order to help prevent allograft rejection of non-self tissue.

One drug which finds use as an immunosuppressant in the United States and other countries is cyclosporin A (CsA). CsA is a cyclic undecapeptide of the general structure:

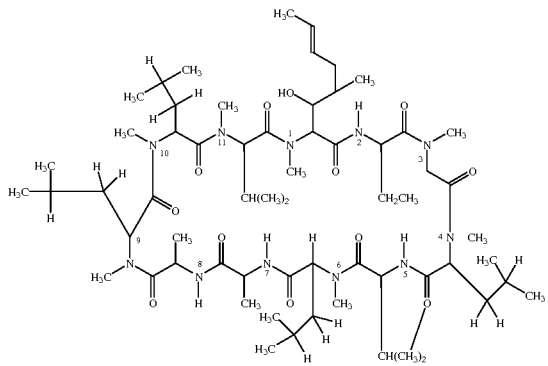

wherein all of the α-amino acid residues that form the cyclic backbone of cyclosporin A are of the L-configuration except α-amino acid 8 which is of the D-configuration. Amino acid residue 1 is derived from an unusual 9 carbon amino acid [2S,3R,4R,6E]-3-hydroxy-4-methyl-2-methylamino-6-octenoic acid. Amino acid residues 1, 3, 4, 6, 9, 10 and 11 are N-methylated on the amide nitrogen atoms of the cyclic backbone of cyclosporin A. Cyclosporin A is described in U.S. Pat. Nos. 4,117,118 (1978) and 4,396,542 (1983).

CsA may have other useful properties such as antibiotic, anti-arthritic and anti-inflammatory activities and may find use in the treatment of other conditions such as diabetes, malaria and autoimmune diseases.

A large number of CsA metabolites that retain the undecapeptide ring have been identified and reported (see Maurer, G.; Loosli, H. R.; Schreier, E.; Keller, B. *Drug Metabolism and Disposition* 1984, 12(1), 120–126, the structures, nomenclature and analytical data of the metabolites are incorporated herein by reference). It is not known what role, if any, these metabolites play in either the desired immunosuppressant activity or any unwanted adverse reactions when CsA is used for the prevention of allograft rejection.

Even though CsA is a highly effective immunosuppressant drug, its use must be carefully managed because the effective dose range is narrow and excessive dosage can result in serious side effects. Renal dysfunction, hypertension, cardiovascular cramps, hirsutism, acne, tremor, convulsions, headache, gum hyperplasia, diarrhea, nausea, vomiting, hepatotoxicity, abdominal discomfort, paresthesia, flushing, leukopenia, lymphoma, sinusitis and gynecomastia have been observed in kidney, heart or liver transplant patients undergoing CsA treatment. Too little CsA can lead to graft rejection.

Management of CsA dosage involves careful control of the level of the drug present in the patient. Because the distribution and metabolism of CsA varies greatly between patients, and because of the wide range and severity of adverse reactions, accurate monitoring of drug level is considered essential.

Laboratory methods for detection of cyclosporin have been developed. These techniques typically involve high performance liquid chromatography (HPLC), radioimmunoassay (RIA) or florescence polarization immunoassay (FPIA). See for example Wolf, B. A.; et al. *Clinical Chem.* 1989, 35(1), 120–124; Vernillet, L.; et al. *Clinical Chem.* 1989, 35(4), 608–611; Ball, P. E.; et al. *Clinical Chem.* 1988, 34(2), 257–260; Schran, H. F.; et al. *Clinical Chem.* 1987, 33(12), 2225–2229; Sanghvi, A.; et al. *Clinical Chem.* 1988, 34(9), 1904–1906; McBride, J. H.; et al. *Clinical Chem.* 1989, 35(8), 1726–1730; Quesniaux, V.; et al. *Clinical Chem.* 1987, 33(1), 32–37.

Each of these techniques has certain limitations with regard to safety and complexity of the procedure and level of specificity for cyclosporins of interest. For example, HPLC requires long sample preparation and/or run times using high cost labor-intensive procedures; RIA presents the well-known hazards of handling radioactive materials; and FPIA, when based on non-specific mono- or polyclonal-antibodies, often fails to distinguish between CsA and its metabolites.

A simple analytical method specific to selected cyclosporins is needed for use in cyclosporin treatment management.

Immunoassay is a technique suited to the requirements of a simple method for measuring the amount of cyclosporin in a sample suspected of containing cyclosporin. However, most available antibodies capable of recognizing cyclosporins of interest also recognize and cross-react with closely related compounds such as cyclosporin metabolites. Because of this cross-reactivity, immunoassays dependent on these antibodies are less specific to cyclosporins of interest than might be desired. Cyclosporin immunoassays dependent on antibodies which cross-react with compounds other than cyclosporins of interest can be improved if the cross-reactive compounds are substantially inactivated toward recognition by the antibodies which recognize the cyclosporins of interest.

The methods and compositions of the present invention relate to a simple, specific immunoassay method for cyclosporins. The methods and compositions of the present invention also related to a method for inactivating cross-reactive compounds in immunoassay methods for cyclosporin.

2. Brief Description of the Related Art

World Patent Application No. 8,602,080 (1986), describes monoclonal antibodies selective for certain cyclosporins. These antibodies are prepared in response to cyclosporins bound to antigenic carriers through a modified amino acid residue such as a (D)-Lysine at position 8 or an (L)-threonine at position 2.

European patent application No. 283,801 (1988), describes a fluorescence immunoassay method and cyclosporin A derivatives used to raise antibodies. Cyclosporin A is linked to an immunogenic carrier via the amino acid side-chain at amino acid residue no. 1.

Cacalano, N. A.; Cleveland, W. L.; Erlanger, B. F. *J. Immunol. Meth.* 1989, 118, 257–263, describes the, presumably but not certainly, random photochemical grafting of cyclosporin A alkyl side-chains onto 4-benzoylbenzoic acid. These grafts are used to couple to immunogenic carriers for antibody preparation.

U.S. Pat. No. 4,727,035 (1988), describes a method of immunoassay for cyclosporins. The method involves either radioiodine or fluorescence immunoassay.

Quesniaux, V. F. J.; Tees, R.; Schreier, M. H.; Wenger, R. M.; Van Regenmortel, M. H. V. *Molecular Immunology* 1987, 24(11), 1159–1168, describes antibodies grown in response to cyclosporin-immunogen conjugates. The conjugates are attached to cyclosporin through a modified side chain on amino acids 2 or 8.

U.S. Pat. Nos. 4,764,503 (1988), 4,639,434 (1987), and 4,384,996 (1983), describe cyclosporins modified at amino acid residue no. 8. These cyclosporins are hydroxylated on the amino acid side-chain and are useful as immunosuppressive drugs.

SUMMARY OF THE INVENTION

One aspect of the present invention relates to methods useful for measuring the amount of cyclosporin in a sample suspected of containing cyclosporin. The method involves the steps of a) combining in an aqueous medium, 1) a sample suspected of containing cyclosporin, 2) cyclosporin conjugated, optionally through a linking group, at one of the alanine nitrogen atoms, which are part of the cyclic backbone of cyclosporin, to a label, and 3) antibodies capable of binding to the cyclosporin label conjugate; and, optionally, b) measuring the amount of the cyclosporin label conjugate bound to the antibodies.

Another aspect of the present invention relates to methods useful for inactivating interfering cross-reactive material in an assay for measuring the amount of cyclosporin in a sample suspected of containing cyclosporin. The method involves the step of combining an assay medium containing the sample with an antibody capable of recognizing the interfering cross-reactive material but substantially incapable of interfering with the assay for measuring the amount of cyclosporin.

Another aspect of the present invention relates to cyclosporin conjugated, optionally through a linking group, at one of the alanine nitrogen atoms, which are part of the cyclic backbone of cyclosporin, to a label. These conjugates are useful in the assay method of the invention.

Another aspect of the present invention relates to cyclosporin conjugated, optionally through a linking group, at one of the alanine nitrogen atoms which are part of the cyclic backbone of cyclosporin, to an immunogenic carrier. These conjugates are useful in raising antibodies for use in an assay method of the invention.

Another aspect of the present invention relates to atiocylosporin conjugated, optionally through a linking group, to a label.

Another aspect of the present invention relates to atiocyclosporin conjugated, optionally through a linking group, to an immunogenic carrier.

Another aspect of the present invention relates to antibodies, which are raised in response to cyclosporin conjugated, optionally through a linking group, at one of the alanine nitrogen atoms, which are part of the cyclic backbone of cyclosporin, to an immunogenic carrier. These antibodies are useful in the assay method of the invention.

Another aspect of the present invention relates to antibodies, which are raised in response to atiocyclosporin conjugated, optionally through a linking group, to an immunogenic carrier. These antibodies are useful in the method of reducing interfering cross-reactive material.

Another aspect of the present invention relates to methods of preparing cyclosporin conjugated, optionally through a linking group, at one of the alanine nitrogen atoms, which are part of the cyclic backbone of cyclosporin, to an immunogenic carrier or a label.

Another aspect of the present invention relates to methods of preparing atiocyclosporin conjugated, optionally through a linking group, to an immunogenic carrier or a label.

Another aspect of the present invention relates to reagents useful for performing a assay method of the invention.

Another aspect of the present invention relates to reagents useful for performing the methods of inactivating interfering cross-reactive material in an assay for cyclosporin.

Another aspect of the present invention relates to kits useful for conveniently performing an assay method of the invention.

Another aspect of the present invention relates to kits useful for conveniently performing the method of inactivating interfering cross-reactive material in an assay for cyclosporin.

DESCRIPTION OF THE SPECIFIC EMBODIMENTS

Methods, compositions, reagents and kits are provided, which are useful in cyclosporin immunoassays. Before proceeding with the description of the specific embodiments a number of terms will be defined.

EMIT®— A trademark of Syva company, 3403 Yerba Buena Road, P.O. Box 49013, San Jose, Calif., 95161-9013, used for a product line of enzyme immunoassays, which are described in U.S. Pat. No. 3,817,837 (1974), the disclosure of which is incorporated herein by.reference. In the patented assays, a sample suspected of containing an analyte is combined in an aqueous medium either simultaneously or sequentially with an analyte-enzyme conjugate and antibody capable of recognizing the analyte and the conjugate. Further details are available in the above referenced and incorporated U.S. Patent.

DEFINITIONS

Linking Group—A linking group is a portion of a structure, which connects 2 or more substructures. A linking group has at least 1 uninterrupted chain of atoms other than hydrogen (or other monovalent atoms) extending between the substructures. The atoms of a linking group and the atoms of a chain within a linking group are themselves connected by chemical bonds.

The number of atoms in a linking group is determined by counting the atoms other than hydrogen. The number of atoms in a chain within a linking group is determined by counting the number of atoms other than hydrogen along the shortest route between the substructures being connected. For example, diphenylmethane has 2 benzene rings connected by a 1 atom linking group, which contains a 1 atom chain; stilbene has 2 benzene rings connected by a 2 atom linking group, which contains a 2 atom chain; 1,2-diphenyl-3-ethylcyclohexane has 2 benzene rings connected by an 8 atom linking group, which contains a 2 atom chain.

Carboxamide Group—A carboxamide group is a portion of a structure, which is comprised of a substructure of the formula:

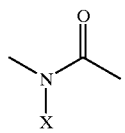

wherein X is hydrogen, alkyl (of less than about 9 carbon atoms), or hydroxyalkyl (of less than about 9 carbon atoms). Preferably, X is hydrogen, or a straight or branched alkyl group, optionally substituted with hydroxy groups, containing primarily, other than hydrogen, less than about 9 carbon atoms, preferably, less than about 7 carbon atoms, more preferably, less than about 5 carbon atoms. Carboxamide groups are typically connected to each other by alkylene chains to form poly(carboxamides) also referred to as poly (peptides). Preferably, the alkylene chains are straight or branched alkyl chains, optionally substituted with hydroxy groups, containing primarily, other than hydrogen, less than about 11 carbon atoms, preferably, less than about 9 carbon atoms, more preferably, less than about 7 carbon atoms.

Non-oxocarbonyl—A group having the general structure of the formula:

other than a ketone or aldehyde, wherein $T_1$ is a chalcogen (oxygen or sulfur) or substituted nitrogen, wherein the nitrogen substituent can be, for example, H or alkyl. Exemplary of non-oxocarbonyl groups are carboxylic acids, esters, amides, carbamates, carbonates, ureas, and so forth, including the sulfur and nitrogen analogs thereof.

Cyclosporin—In the context of the present invention, a cyclosporin group is a natural or synthetic cyclosporin or derivative. Cyclosporin groups are cyclic, undecapeptides of the general formula:

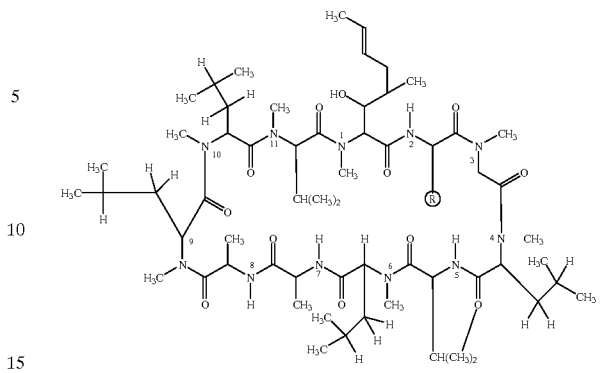

wherein R is a linear or branched alkyl group, optionally substituted with hydroxy groups, containing primarily, other than hydrogen, less than about 9 carbon atoms, preferably less than about 7 carbon atoms. For example, R is —CH$_2$CH$_3$ in cyclosporin A, R is —CH$_3$ in cyclosporin B, R is —CH(OH)CH$_3$ in cyclosporin C, and R is —CH(CH$_3$)$_2$ in cyclosporin D. Suitable cyclosporins include cyclosporin A, cylosporin B, cylosporin C, cylosporin D, cylosporin E, cylosporin F, cylosporin G, cylosporin H, cylosporin I.

The exact structure of cyclosporin may vary in minor ways from example to example. For instance, changes in the structure of the side chains of amino acid residues 2–6 and 9–11 are contemplated within the scope of the invention. Further, changes in the structure of the pendant substituent on the amide nitrogen atoms of amino acid residues 2–6 and 9–11 are contemplated within the scope of the invention. Further still, changes in the absolute stereochemical configuration of the α-carbon atom of amino acid residues 2–11 are contemplated within the scope of the invention.

Within the scope of the invention, amino acid residue no. 1 will remain substantially unmodified. Further, one or both of amino acid residues no. 7 and 8 will be a d-alanine, l-alanine or a mixture thereof.

Alanine nitrogen atom of cyclosporin—Each of the cyclic peptide units of a cyclosporin molecule contain an amide nitrogen atom as part of the backbone of the cyclosporin ring. Within the context of the present invention, the amide nitrogen atoms of alanine residues are alanine nitrogen atoms of cyclosporin. For example, these are nitrogen atoms of amino acid residues no. 7 and 8 in cyclosporin A, C, and D, as well as, residues no. 2, 7, and 8 in cyclosporin B.

Carbon atom no. 6 of cyclosporin amino acid residue no. 1—The amino acid residue at position no. 1 of cyclosporin A (CsA) is a condensed form of the free amino acid [2S,3R,4R,6E]-3-hydroxy-4-methyl-2-methylamino-6-octenoic acid. See Wenger, R. U.S. Pat. No. 4,396,542 (1983); Wenger, R. M. Helvetica Chim. Acta 1983, 66(7), 2308–2321. This unique amino acid is also referred to as N-methyl-(4R)-4-but-2E-en-1-yl-4-methyl-(L)threonine (MeBmt). See Wenger, R.; et al. U.S. Pat. No. 4,639,434 (1987). The structure and numbering system used for both the condensed and free forms of MeBmt are shown in the formula:

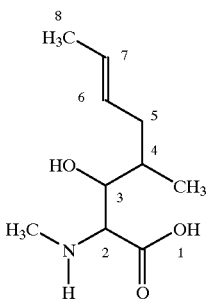

Atiocyclosporin—In one of its composition aspects, the present invention relates to compounds prepared by cleaving cyclosporin amino acid residue no. 1 at the bond or bonds connecting carbon atoms no. 6 and 7 and conjugating the resulting cleaved product, optionally through a linking group, to a label, immunogenic carrier, small organic molecule, or the like. When the side chain of amino acid no. 1 is cleaved at the carbon atom no. 6-carbon atom no. 7 bond, carbon atoms no. 7 and 8 are removed and a functionality is introduced on carbon atom no. 6.

The new functional group on carbon atom no. 6 is any functional group, which permits attachment of carbon atom no. 6 to a linking group, label, immunogenic carrier, small organic molecule, or the like. Such functional groups can include heteroatom containing groups, preferably, oxocarbonyls or non-oxocarbonyls.

The resulting cyclosporin, wherein carbon atom no. 7 and 8 of cyclosporin amino acid residue no. 1 have been removed and a functional group has been introduced on carbon atom no. 6, is referred to as an atiocyclosporin.

Atiocyclosporin carboxaldehyde—In the context of the present invention, it is preferred that the side chain of cyclosporin amino acid residue no. 1 be oxidatively cleaved at the olefinic bond connecting carbon atom no. 6 and 7 to form a cyclosporin wherein carbon atom no. 7 and 8 of the side chain of amino acid residue no. 1 have been removed and replaced by an oxygen atom to form an aldehyde function at carbon atom no. 6 of cyclosporin amino acid residue no. 1.

The above described preferred compound is referred to as atiocyclosporin carboxaldehyde, the structure of which is shown in the formula:

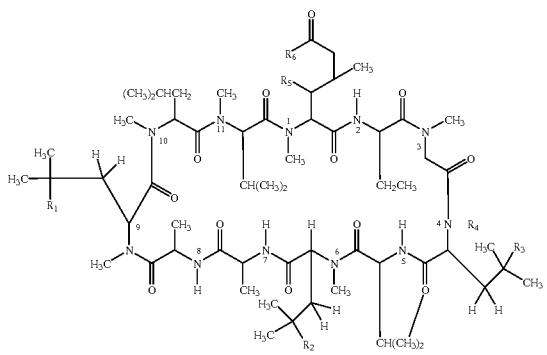

wherein $R_1$, $R_2$, and $R_3$ are H or hydroxyl, at least one being hydroxyl. $R_4$ is H or methyl. $R_5$ is hydroxyl trialkylsiloxy or acyloxy and $R_6$ is H. More preferably, $R_1$ and $R_5$ are hydroxyl, $R_2$, $R_3$, and $R_6$ are H, and $R_4$ is methyl. This most preferred embodiment is the atiocyclosporin carboxaldehyde formed from cyclosporin A metabolite M-1.

Interfering cross-reactive material—materials other than cyclosporins of interest, which may be recognized by antibodies capable of recognizing the cyclosporins of interest, are interfering cross-reactive material. Such material can include compounds related to the cyclosporins of interest. In particular, metabolites of cyclosporin, which retain the undecapeptide ring, are common interfering cross-reactive material. The above incorporated work of Maurer; et al. describes a number of cyclosporin metabolites. The structures of 8 common metabolites are shown below. These 8 metabolites are illustrative, but not exclusive, examples of interfering cross-reactive material. The present invention in one of its most preferred aspects involves cyclosporin A metabolite M-1 as an interfering cross-reactive material.

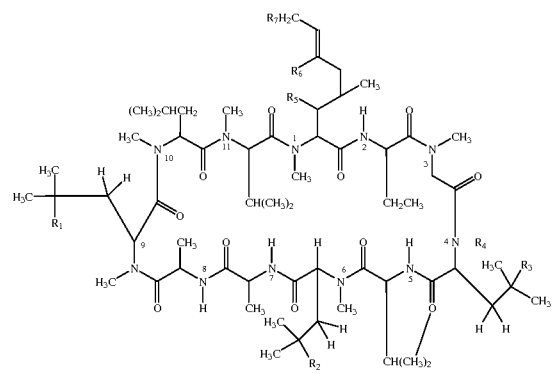

| METABOLITE | $R_1$ | $R_2$ | $R_3$ | $R_4$ | $R_5$ | $R_6$ | $R_7$ |
|---|---|---|---|---|---|---|---|
| M1  | OH | H  | H  | $CH_3$ | OH | H | H  |
| M8  | OH | H  | H  | $CH_3$ | OH | H | OH |
| M9  | OH | OH | H  | H      | OH | H | H  |
| M10 | OH | H  | OH | $CH_3$ | OH | H | H  |
| M16 | OH | OH | H  | $CH_3$ | OH | H | H  |
| M17 | H  | H  | H  | $CH_3$ | OH | H | OH |
| M18 | H  | H  | H  | $CH_3$ | *  | * | OH |
| M21 | H  | H  | H  | H      | OH | H | H  |

*$R_5$ and $R_6$ are taken together with an oxygen atom to form a tetrahydrofuranyl ring and the olefinic bond is saturated Organic radical—An organic radical is a residue of a large organic molecule or it is a residue of a small organic molecule. Preferably, organic radicals are comprised of immunogenic carriers and labels, together with any linking groups. An organic radical can have any number of atoms. Preferably the organic radical will contain at least 5 atoms including hydrogen.

Residue of a small organic molecule—A residue of a small organic molecule is a group derived by attachment of a small organic molecule. A small organic molecule is a compound of molecular weight less than about 2,000, and preferably about 100 to 1,000, more preferably about 300 to 600, such as biotin, fluorescein, rhodamine and other dyes, tetracycline and other protein binding molecules, and haptens, and the like. The small organic molecule will be capable of attachment (conjugation), optionally through a linking group, to a cyclosporin at one of the alanine nitrogen atoms of the cyclosporin. When the small organic molecule is so attached, it becomes a residue of a small organic molecule.

Residue of a large organic molecule—A residue of a large organic molecule is a group having a molecular weight greater than 2,000 and includes poly(amino acids), lipopolysaccharides, particles, and the like. Such a group can, among other things, be a label or an immunogenic carrier.

Poly(amino acid)—A poly(amino acid) is a polyamide formed from amino acids. Poly(amino acids) are also referred to as polypeptides and will generally range from about 2,000 molecular weight, having no upper molecular weight limit, normally being less than 10,000,000, usually not more than about 600,000 daltons. There will usually be different ranges, depending on whether an immunogenic carrier or an enzyme is involved.

Immunogenic carrier—An immunogenic carrier is a group which, when conjugated, optionally through a linking group, to an alanine nitrogen atom of cyclosporin and injected into a mammal, will induce an immune response and elicit the production of antibodies that bind to cyclosporin. Immunogenic carriers are also referred to as antigenic carriers and by other synonyms common in the art.

The molecular weight of immunogenic carriers typically range from about 2,000 to $10^7$, usually from about 20,000 to 600,000, and more usually from about 25,000 to 250,000 molecular weight. There will usually be at least about one cyclosporin group per 150,000 molecular weight, more usually at least one group per 50,000 molecular weight, preferably at least one group per 25,000 molecular weight.

Various protein types may be employed as the poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums, such as gum arabic, agar, and so forth. The polysaccharide can also contain polyamino acid residues and/or lipid residues.

The immunogenic carrier can also be a poly(nucleic acid) either alone or conjugated to one of the above mentioned poly(amino acids) or polysaccharides.

The immunogenic carrier can also be a particle. The particles are generally at least about 0.02 microns and not more than about 100 microns, usually at least about 0.05 microns and less than about 20 microns, preferably from about 0.3 to 10 microns diameter. The particle may be organic or inorganic, swellable or non-swellable, porous or non-porous, preferably of a density approximating water, generally from about 0.7 to 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, staphylococcus aureus, E. coli*, viruses, and the like. The particles can also be particles comprised of organic and inorganic polymers, liposomes, latex particles, phospholipid vesicles, chylomicrons, lipoproteins, and the like.

The polymers can be either addition or condensation polymers. Particles derived therefrom will be readily dispersible in an aqueous medium and may be adsorptive or functionalizable so as to bind (conjugate) to a cyclosporin group, either directly or indirectly through a linking group.

The particles can be derived from naturally occurring materials, naturally occurring materials which are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The particles will usually be polyfunctional and will be bound to or be capable of binding (being conjugated) to a cyclosporin group, optionally through a linking group. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.* 1970, 245, 3059, the linking methods of which are incorporated herein by reference.

Label—A label is any molecule, which produces or can be induced to produce a signal. The label may be conjugated to an analyte or an antibody, or to another molecule such as a receptor or a molecule that can bind to a receptor such as a ligand, particularly a hapten. In the subject invention, the label can be a member of the signal producing system, as defined below, that includes a signal producing means.

The label may be isotopic or nonisotopic, preferably nonisotopic. By way of example and not limitation, the label can be a part of a catalytic reaction system such as enzymes, enzyme fragments, enzyme substrates, enzyme inhibitors, coenzymes, or catalysts; part of a chromogen system such as fluorophores, dyes, chemiluminescers, luminescers, or sensitizers; a dispersible particle that can be non-magnetic or magnetic, a solid support, a liposome, a ligand, a receptor, a hapten radioactive isotope, and so forth.

Enzymes, enzyme fragments, enzyme inhibitors, enzyme substrates, and other components of enzyme reaction systems can be used as labels. Where any of these components is used as a label, a chemical reaction involving one of the components is part of the signal producing system.

When enzymes are employed, molecular weights of the label typically range from about 10,000 to 600,000, more usually from about 10,000 to 300,000, and the involved reactions will be, for the most part, hydrolysis or redox reactions.

Coupled catalysts can also involve an enzyme with a non-enzymatic catalyst. The enzyme can produce a reactant, which undergoes a reaction catalyzed by the non-enzymatic catalyst or the non-enzymatic catalyst may produce a substrate (includes coenzymes) for the enzyme. A wide variety of non-enzymatic catalysts, which may be employed are found in U.S. Pat. No. 4,160,645 (1979), the appropriate portions of which are incorporated herein by reference.

The enzyme or coenzyme employed provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 columns 19 to 23, and U.S. Pat. No. 4,318,980, columns 10 to 14, which disclosures are incorporated herein by reference.

A number of enzyme combinations are set forth in U.S. Pat. No. 4,275,149, columns 23 to 28, which combinations can find use in the subject invention. This disclosure is incorporated herein by reference.

Of particular interest are enzymes, which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference.

When a single enzyme is used as a label, such enzymes that may find use are hydrolases, transferases, lyases, isomerases, ligases or synthetases and oxidoreductases, preferably, hydrolases. Alternatively, luciferases may be used such as firefly luciferase and bacterial luciferase. Primarily, the enzymes of choice, based on the I.U.B. classification are: Class 1. Oxidoreductases and Class 3. Hydrolases; particularly in Class 1, the enzymes of interest are dehydrogenases of Class 1.1, more particularly 1.1.1, 1.1.3, and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, β-glucosidase and lysozyme are illustrative.

Those enzymes, which employ nicotinamide adenine dinucleotide (NAD) or its phosphate (NADP) as a cofactor, particularly the former, can be used. One preferred enzyme is glucose-6-phosphate dehydrogenase, preferably, NAD-dependent glucose-6-phosphate dehydrogenase.

The label can also be fluorescent either directly or by virtue of fluorescent compounds or fluorescers bound to a particle or other molecule in conventional ways. The fluorescent labels will be bound to, or functionalized to render them capable of binding (being conjugated) to, optionally through a linking group, cyclosporin or antibodies or receptors for cyclosporin.

The fluorescers of interest will generally emit light at a wavelength above about 350 nm, usually above about 400 nm and preferably above about 450 nm. Desirably, the fluorescers have a high quantum efficiency, a large Stokes shift, and are chemically stable under the conditions of their conjugation and use. The term luminescent label is intended to include substances that emit light upon activation by electromagnetic radiation, electro chemical excitation, or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes imines, anthracenes, oxacarboxyanine, merocyanine, 3-aminoequilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates, oxides, and salts. Exemplary fluorescers are enumerated in U.S. Pat. No. 4,318,707, columns 7 and 8, the disclosure of which is incorporated herein by reference.

Energy absorbers or quenchers can be employed either separately or in conjunction with one another. The absorber or quencher can additionally be bound to a solid insoluble particle of at least about 50 nm in diameter. When the distance between the absorber and the quencher resulting from specific binding events (such as antibody-antigen binding) too small, the fluorescence of the absorber is quenched by the quencher. The quencher may be the same or different, usually different, from the fluorescer.

An alternative source of light as a detectable signal is a chemiluminescent source, and, therefore, a label can be a chemiluminescent compound. The chemiluminescent source involves a compound, which becomes electronically excited by a chemical reaction and may then emit light which serves as the detectable signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benzo analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with geridinium esters, dioxetanes, and oxalates, usually oxalyl active esters, e.g., p-nitrophenyl and a peroxide, e.g., hydrogen peroxide, under basic conditions. Alternatively, luciferins may be used in conjunction with luciferase or lucigenins.

Conjugate—A conjugate is a molecule comprised of two or more subunits bound together, optionally through a linking group, to form a single structure. The binding can be made either by a direct connection (e.g. a chemical bond) between the subunits or by use of a linking group. For example, in one context of the present invention, cyclosporin conjugated, optionally through a linking group, at an alanine nitrogen atom of cyclosporin to an enzyme is a cyclosporin-enzyme conjugate. A composition described as comprising subunit A conjugated, optionally through a linking group, to subunit B is a composition wherein subunit A is bound, optionally through a linking group, to subunit B.

Conjugation—Conjugation is any process wherein two subunits are linked together to form a conjugate. The conjugation process can be comprised of any number of steps.

Receptor—A receptor is any compound or composition capable of recognizing a particular spatial and polar organization of a molecule. These organized areas of a molecule are referred to as epitopic or determinant sites. Illustrative naturally occurring receptors include antibodies, enzymes, fab fragments, poly(nucleic acids), complement component, i.e. thyroxine binding globulin, lectins, protein A, and the like. Receptors are also referred to as antiligands. A natural receptor exists that binds specifically to cyclosporin.

Ligand—A ligand is any organic molecule for which a receptor naturally exists or can be prepared. For example, in one context of the present invention, cyclosporin is a ligand and the present invention provides receptor antibodies for cyclosporin. In another context of the present invention, cyclosporin can be conjugated, optionally through a linking group, at an alanine nitrogen atom of cyclosporin to a second ligand. When cyclosporin is linked in this manner to a second ligand (cyclosporin-ligand conjugate), receptors capable of recognizing the second ligand will recognize the cyclosporin-ligand conjugate.

Hapten—Haptens are capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier. Haptens are a subset of ligands.

For example, in one context of the present invention, cyclosporin is a hapten. When cyclosporin is conjugated, optionally through a linking group, at one of the alanine nitrogen atoms of cyclosporin to an immunogenic carrier, antibodies capable of recognizing cyclosporin can be prepared. In another context of the present invention, cyclosporin is conjugated, optionally through a linking group, at one of the alanine nitrogen atoms of cyclosporin to a second hapten. When cyclosporin is conjugated in this fashion to a second hapten (cyclosporin-hapten conjugate), antibodies capable of recognizing the second hapten and antibodies capable of recognizing cyclosporin will bind to the cyclosporin-hapten conjugate.

Member of a specific binding pair—A member of a specific binding pair (sbp member) is one of two different molecules, having an area on the surface or in a cavity, which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs, such as biotin-avidin, hormones-hormone receptors, nucleic acid duplexes, IgG-protein A, DNA-DNA, DNA-RNA, and the like, are not immunological pairs but are specific binding pairs.

Support or surface—A support or surface is a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Other materials, which can be employed, are described above in the definition of immunogenic carrier particles and below in the definition of a signal producing system.

Binding of sbp members to the support or surface may be accomplished by well-known techniques, commonly available in the literature, and described above in the definition of immunogenic carrier particles. The surface can have any one of a number of shapes, such as strip, rod, particle, including bead, and the like.

The surface will usually be polyfunctional or be capable of being polyfunctionalized or be capable of binding an sbp member through specific or non-specific covalent or non-covalent interactions. A wide variety of functional groups for linking are described in the definition of immunogenic carrier particles.

The length of a linking group to the sbp member may vary widely, depending upon the nature of the compound being linked, the effect of the distance between the compound being linked and the support on the assay and the like. The sbp member will be substantially bound to the outer surface of the support.

Signal producing system—The function of the signal producing system is to produce a product, which provides a detectable signal related to the amount of bound and/or unbound label.

The signal producing system may have one or more components, at least one component being a label. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes, which absorb light in the ultraviolet or visible region, phosphors, or fluorescers.

The signal producing means is capable of interacting with the label to produce a detectable signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The signal producing system including the label can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/mL, and composed of material that can be transparent, partially transparent, or opaque. Generally, particles utilized as a label will have similar characteristics to those described above in the definitions of an immunogenic carrier and a support or surface.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver, or copper sulfides or metal oxides, such as iron or copper oxide.

Fluoresceinated latex particles are taught in U.S. Pat. No. 3,853,987 and are available commercially as Covaspheres from Covalent Technology Corp.

Measuring the amount of cyclosporin—Quantitative, semiquantitative, and qualitative methods as well as all other methods for determining cyclosporin are considered to be methods of measuring the amount of cyclosporin. For example, a method that merely detects the presence or absence of cyclosporin in a sample suspected of containing cyclosporin is considered to be included within the scope of the present invention.

Synonymg for the phrase "measuring the amount of cyclosporin", which are contemplated within the scope of the present invention include, but are not limited to, detecting, measuring, or determining cyclosporin; detecting, measuring, or determining the presence of cyclosporin; and detecting, or determining the amount of cyclosporin.

Substantially capable or substantially incapable of binding to or recognizing—refers to an amount of binding or recognizing, or lack thereof between molecules in an assay mixture under particular assay conditions. In its broadest aspect, the differentiation between one molecule's incapability of binding or recognizing another molecule and capability of binding or recognizing a third molecule is sufficient to allow a meaningful assay to be conducted under a particular set of assay conditions, which includes the relative concentrations of the molecules. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration of the molecules.

Sample suspected of containing cyclosporin—Any sample, which is reasonably suspected of containing cyclosporin, can be analyzed by the method of the present invention. Such samples can include human, animal, or man-made samples. The sample can be prepared in any convenient medium, which does not interfere with the assay. Typically, the sample is an aqueous solution or a natural fluid, preferably, urine, whole blood, serum, plasma, or saliva more preferably, whole blood.

Sample pretreatment—Optionally, the sample suspected of containing cyclosporin can be pretreated. Pretreatment is any step designed to make the target analyte more readily available to one or more of the assay reagents. Preferably, samples to be analyzed by the method of the present invention will be pretreated to lyse cells that may be present, to precipitate proteins that may be present, and to solubilize cyclosporin that may be present. Such pretreatment may include treatment of the sample with an organic solvent, preferably, an alcohol, more preferably, methanol.

SPECIFIC EMBODIMENTS

One aspect of the present invention relates to compositions comprising a cyclosporin conjugated to an organic radical, optionally through a linking group, at an alanine nitrogen atom of cyclosporin. Preferably, cyclosporin A is conjugated, optionally through a linking group of less than about 50, preferably, less than about 35, more preferably, less than about 20 atoms other than hydrogen having a chain of not more than about 35, preferably not morn than 25, more preferably not more than 15, atoms in length, at the alanine nitrogen atom of cyclosporin A amino acid residues no. 7 and/or 8. The organic radical can be a group of molecular weight greater than about 2,000, preferably greater than about 5,000, or a residue of a small organic molecule, such as a ligand, hapten or biotin. Preferably, the group of molecular weight greater than 2,000 is a poly (amino acid). More preferably, the poly(amino acid) is an immunogenic carrier such as keyhole limpet hemocyanin (KLH), bovine serum albumin (BSA), or bovine gamma globulin (BGG), or it is an enzyme such as glucose-6-phosphate dehydrogenase (G6PDH).

The linking group, when present, will preferably be comprised of a hydroxyalkane chain of the formula: $-(CH_2)_nO-$, wherein the alanine nitrogen atom of cyclosporin is conjugated to a carbon atom of the hydroxyalkane and the organic radical is conjugated to the oxygen atom, and n is an integer in the range of about 1 to 6, preferably, 2 to 4, more preferably, n is 2. More preferably, the hydroxyalkane linking group will be extended at the oxygen atom by from about 1 to about 3 carboxamide groups linked together by alkylene chains. In the extended case, the organic radical is bound to one end of the carboxamide extending group and the oxygen atom of the hydroxyalkane group is bound to the other end of the carboxamide extending group.

Alternatively, when present, the linking group will be comprised of a carboxybenzyl group of the formula:

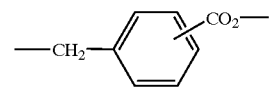

wherein the alanine nitrogen atom of cyclosporin is conjugated to the benzylic carbon atom and the organic radical is bound to an oxygen atom of the carboxy group. The carboxy group is preferably ortho or para, more preferably para, to the benzylic carbon. More preferably, the carboxy benzyl group will be extended at an oxygen atom of the carboxy group by from about 1 to about 3 carboxamide groups linked together by alkylene chains. In the extended case, the organic radical is bound to one end of the carboxamide extending group and the oxygen atom of the carboxy group is bound to the other end of the carboxamide extending group.

More preferably, the linking group is selected from the group consisting of:

(I)

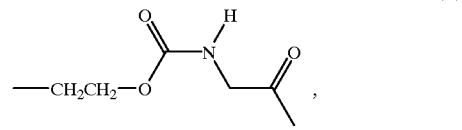

(II)

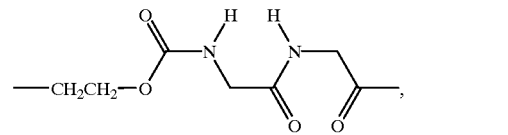

(III)

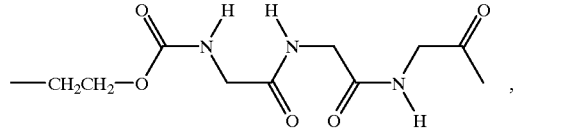

(IV)

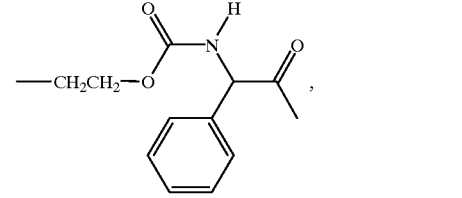

(V)

-continued
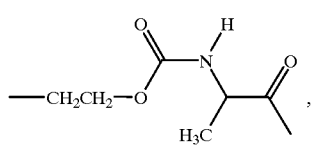
(VI)
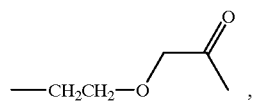
(VII)
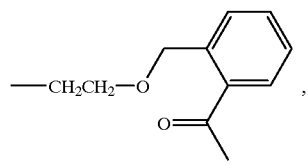
(VIII)
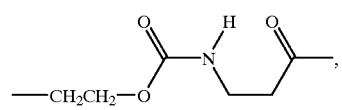
(IX)
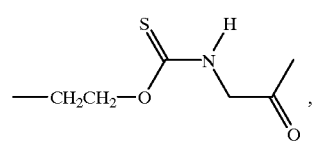
(X)
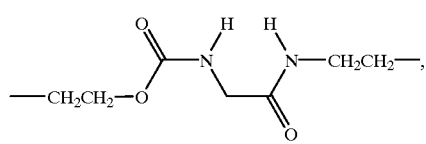
(XI)
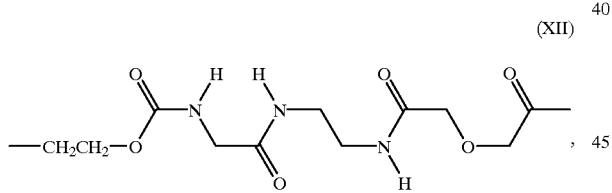
(XII)
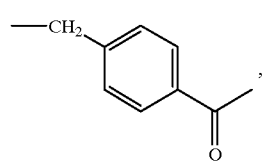
(XIII)
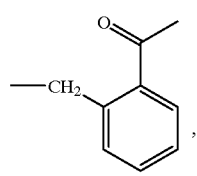
(XIV)
-continued
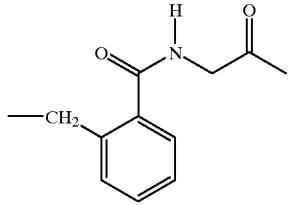
(XV)
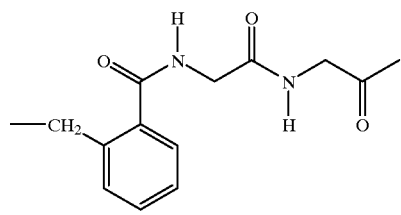
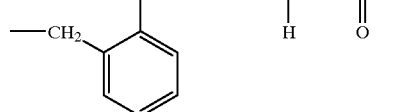
(XVI)
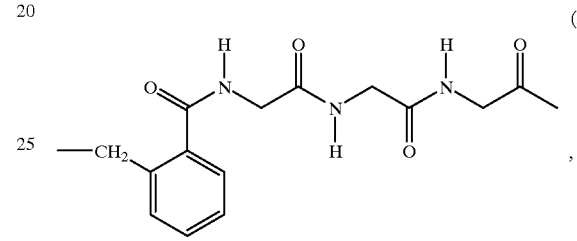
(XVII)
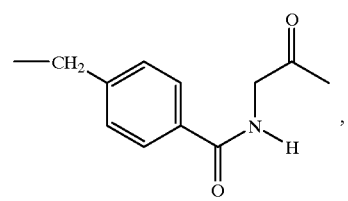
(XVIII)
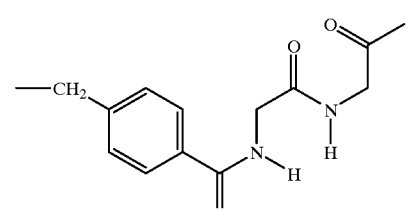
(XIX)
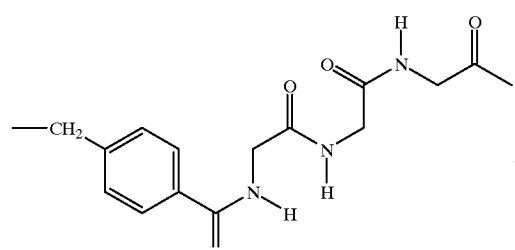
(XX)
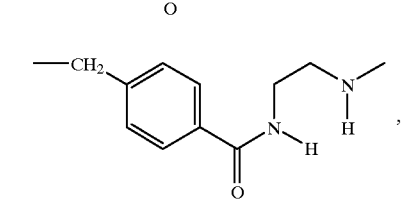
(XXI)

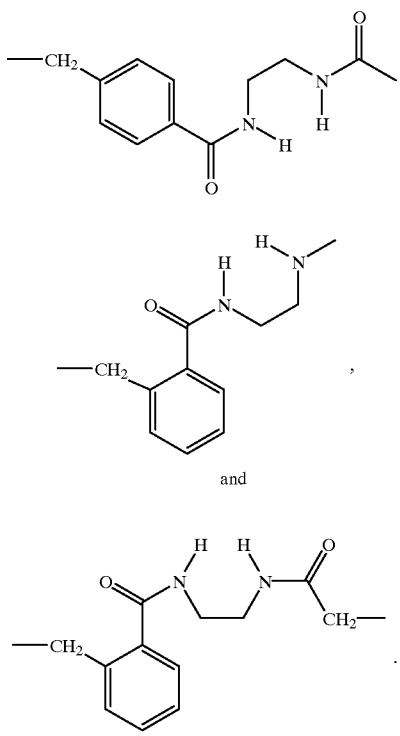

(XXII), (XXIII)

and (XXIV)

Because cyclosporins are cyclic undecapeptides, the alanine nitrogen is part of an amino acid residue. Preferably, the alanine nitrogen is part of cyclosporin amino acid residues no. 7 or 8. More preferably, if the linking group is comprised of an optionally carboxamide extended, hydroxyalkane chain, then the alanine nitrogen is part of cyclosporin amino acid residue no. 7 and if the linking group is comprised of an optionally carboxamide extended carboxybenzyl group, then the alanine nitrogen is part of cyclosporin an amino acid residue chosen from residues no. 7 or 8.

When the organic radical is an immunogenic carrier, suitably it may be an immunogenic poly (amino acid), lipopolysaccharide, particle, and the like. A mixture of is preferred that it is a poly(amino acid). More preferably, it is keyhole limpet hemocyanin (KLH) or bovine serum albumin (BSA). When the organic radical is an immunogenic carrier, it is further preferred that the linking group is a carboxybenzyl group. More preferably, the carboxybenzyl group will be extended by from about 1 to about 3 carboxamide groups linked together by alkylene chains.

One of the preferred compositions contemplated by the present invention is cyclosporin A conjugated at the alanine nitrogen atom of amino acid residue no. 7 and cyclosporin A conjugated at the alanine nitrogen atom of amino acid residue 8 through the linking group of Formula (XIX) to keyhole limpet hemocyanin.

When the organic radical is a label, the type of label depends on the type of assay to be conducted. For enzyme immunoassays the label is an enzyme. Preferably, for homogeneous enzyme immunoassays, it is glucose-6-phosphate dehydrogenase. When the organic radical is a label, it is further preferred that the linking group is a hydroxyalkane group. More preferably, the hydroxyalkane group is extended by from about 1 to about 3 carboxamide groups.

Another of the preferred compositions contemplated by the present invention is cyclosporin A conjugated at the alanine nitrogen atom of amino acid residue no. 7 through the linking group of Formula (II) to glucose-6-phosphate dehydrogenase.

In another aspect, the present invention relates to methods of preparing cyclosporin conjugated, optionally through a linking group, at one of the alanine nitrogen atoms, which are part of the cyclic backbone of cyclosporin to an organic radical. The method comprises the steps of:

a) reacting an optionally protected cyclosporin with a base, which is sufficiently basic to deprotonate a secondary amide, b) reacting the compound of a) with an alkylating agent to form a cyclosporin conjugated at one of its amide nitrogen atoms of its cyclic backbone to a linking group, c) optionally extending the length of the linking group of the compound of b) by adding carboxamide groups to form a cyclosporin conjugated at one of the amide nitrogen atoms of its cyclic backbone to a carboxamide extended linking group, d) removing any protecting groups from the compound of b) or c) to form cyclosporin conjugated at one of the alanine nitrogen atoms of its cyclic backbone to a linking group or to a carboxamide extended linking group (cyclosporin-linking group conjugate), e) optionally activating a functional group on the cyclosporin-linking group conjugate of d) to form a cyclosporin conjugated at one of its alanine nitrogen atoms of its cyclic backbone to an activated linking group (cyclosporin-activated linking group conjugate), and f) optionally reacting the cyclosporin-activated linking group conjugate of e) with a small organic molecule, or a compound of molecular weight greater than 2,000 to form cyclosporin conjugated, optionally through a linking group, at one of the alanine nitrogen atoms to an organic radical, wherein the organic radical is a residue of a small organic molecule, or a group of molecular weight greater than 2,000.

Preferably, the protecting group of a) will be a hydroxy protecting group, which is stable under strong base conditions but easily removable under other mild conditions. Such groups are well known in the art and will not be detailed. However, a detailed recitation of such groups and the conditions necessary for their preparation and later removal can be found in Greene, T. W. "Protective Groups in Organic Synthesis" (Wiley-Interscience, NY, 1981) page 1, paragraph 1, and pages 10–72 of which are incorporated herein by reference and McOmie, J. F. W., Ed. "Protective Groups In Organic Chemistry" (Plenum Press, NY, 1973) pages 96–120 of which are incorporated herein by reference. Such groups include methyl, t-butyl, allyl, benzyl, triarylmethyl, silyl, and tetrahydropyranyl ethers; acetals, ketals, acetates, benzoates, p-nitrobenzoates, formates; trifluoro-, chloro-, methoxy-, and phenoxy-acetates; carbonates, and the like. More preferably, the protecting group will be based on an alkyl silane. Still more preferably, it will be trimethylsilyl. Trimethylsilyl (TMS) protected CsA (TMS-CsA) is shown in Formula (XXV):

(XXV)

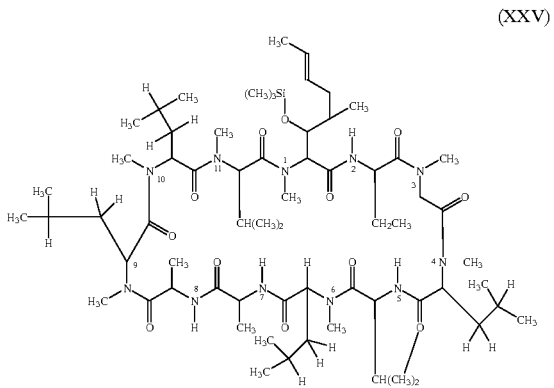

Silation reaction (described in detail in the incorporated material of Greene at pages 39–50) are typically performed in mixed solvents such as an amine/haloalkane mixture. Preferably, a trialkylamine or pyridine mixed with dichloromethane, more preferably, pyridine/dichloromethane. The reaction is performed under an inert atmosphere such as nitrogen, argon, helium, and the like. The reaction typically requires between 1 minute and 24 hours, preferably, 30 minutes and 18 hours. Reaction temperatures are between −10° C. and 100° C., preferably, 0° C. and 50° C., more preferably, 20° C. and 25° C.

Preferably, the base used in step a) will be of sufficient base strength to deprotonate a secondary amide group, which is part of a poly(amino acid). Such bases are well known in the art and will not be detailed. Preferably, the base will be an alkali metal anion (Group 1A salt of a hydride or organic anion) such as a metal hydride, alkyl or amide, including methyl lithium, butyl lithium, lithium hydride, potassium hydride, lithium diisopropyl amide, lithium cyclohexyl isopropyl amide, and the like. More preferably, the base will be a metal hydride base such as sodium, lithium or potassium hydride.

The deprotonation reaction is conducted at −78° C. to 100° C., preferably, −10° C. to 40° C., more preferably, 0° C. to 20° C. The solvent for such reactions is an inert organic solvent such as aliphatic hydrocarbons and aromatic hydrocarbons, for example, benzene, toluene or hexane. Optionally, a metal ion chelator suitable for complexation of Group 1A cations such as a crown ether, β-dicarbonyl compound, or a poly(alkylene oxide) is added to the solvent. Preferably, a crown ether such as 18-crown-6 or 15-crown-5 will be used in an aromatic hydrocarbon solvent, more preferably, 15-crown-5 ether is used in toluene. The reaction is typically performed under an inert atmosphere for between 1 minute and 24 hours, preferably, 10 minutes and 12 hours, more preferably, 10 minutes and 2 hours.

Preferably, the alkylating group of b) will be an α-haloalkylbenzoic acid ester or an epoxide.

More preferably, if the compound to be prepared has a carboxybenzyl linking group, then the alkylating group will be of Formula (XXVI):

(XXVI)

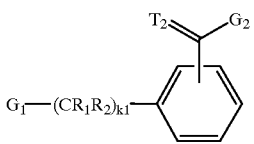

$R_1$ and $R_2$ in Formula (XXVI) are each independently H, or alkyl, of less than about 7 carbon atoms, preferably, H or methyl, more preferably, H.

$G_1$ in Formula (XXVI) is a halogen atom, preferably, bromine, chlorine or iodine, more preferably, a bromine atom.

$T_2$ in Formula (XXVI) is O, S or $NR_3$ wherein $R_3$ is H or alkyl of less than about 7 carbon atoms, preferably, O or S, more preferably, O.

The value of $k_1$ in Formula (XXVI) is from 1 up to about 4, preferably up to about 2, more preferably, $k_1$ is 1.

$G_2$ in Formula (XXVI) is $OR_4$ or $SR_5$ wherein $R_4$ and $R_5$ are protecting groups for the corresponding oxygen, nitrogen or sulfur carbonyl functions selected depending on the nature of $T_2$ and $G_2$. Protecting groups for these functional groups are described in Greene, T. W. "Protective Groups in Organic Synthesis" (Wiley-Interscience, NY, 1981) page 1, paragraph 1, pages 154–192, 209–210, and 249–278 of which are incorporated herein by reference; and McOmie, J. F. W., Ed. "Protective Groups In Organic Chemistry" (Plenum Press, NY, 1973) pages 183–210, 286–295, and 404–412 of which are incorporated herein by reference; and will not be detailed. Preferably, $G_2$ is $OR_4$, wherein $R_4$ is alkyl of less than about 7 carbon atoms, more preferably, $R_4$ is methyl.

Still more preferably, if the compound to be prepared has a carboxybenzyl linking group, then the alkylating agent will be an ortho- or para-α-halomethylbenzoic acid, alkyl (of less than about 7 carbon atoms) ester. Preferably, the product of the alkylation with the α-halomethylbenzoic acid, alkyl ester will be a cyclosporin conjugated at one of the alanine nitrogen atoms of cyclosporin amino acid residues no. 7, and 8, to an ortho- or para-carboxybenzyl, alkyl ester group.

More preferably, if the compound to be prepared has a hydroxyalkane linking group, then the alkylating group will be of Pormula (XXVII):

(XXVII)

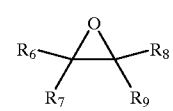

$R_6$, $R_7$, and $R_9$ in Formula (XXVII) are each independently H, alkyl of less than about 7 carbon atoms, preferably, H or methyl, more preferably, H.

Still more preferably, if the compound to be prepared has a hydroxyalkane linking group, then the alkylating agent will be an alkyl epoxide of less than about 7 carbon atoms such as ethylene oxide, propylene oxide, and the like. Preferably, the product of the alkylation with ethylene oxide will be a cyclosporin conjugated at the alanine nitrogen atom of cyclosporin amino acid residue no. 7 to a two carbon chain terminated in a hydroxy group.

The alkylation reagent is typically added to the reaction mixture after the time, described above, for the deprotonation. After addition of the alkylation reagent, the reaction is continued for between 1 minute and 48 hours, preferably, 1 hour and 36 hours, more preferably, 12 hours and 24 hours.

Preferably, the optional carboxamide chain extension step c) will be a standard method of poly(amino acid) synthesis. Such steps are common in the art and will not be detailed. However, a summary of such steps can be found in White, A.; et al. "Principles of Biochemistry" (McGraw-Hill, N.Y., 1978), pages 92–95 of which are incorporated herein by reference.

Generally, any amino, hydroxyl, carboxyl, or other groups, which are not to be reacted, are protected (as described in the above referenced works of Greene and McOmie). Protecting groups include benzyloxycarbonyl, triphenylmethyl, tertiary butyloxycarbonyl, phthaloyl, trifluoroacetyl, benzyl, p-toluenesulfonyl, saturated lower alkyl, benzyl ester, tertiary butyl ester, acetyl, and the like. The unprotected carboxyl group to be reacted is activated by reaction with a coupling reagent to form an activated ester group. Such coupling agents include dicyclohexylcarbodiimide (DCC), isobutyl chloroformate, N,N'-carbonyldiimidazole, p-nitrophenol/DCC, and the like. The activated ester is then reacted with an amino compound to form the carboxamide chain extended compound of c).

More preferably, the carboxamide chain extension step involves reaction of the compound of b) with an isocyanate or thio isocyanate. Typically, the compound to be chain extended is allowed to react with an organometallic catalyst such as an alkyl metal alkoxide in an aliphatic or aromatic, hydrocarbon solvent and an isocyanate or thio isocyanate, saturated alkyl (of less than about 7 carbon atoms) ester is added. Preferably the catalyst will be a trialkyltin complex, more preferably, tributyltin ethoxide. The preferred solvents are aromatic hydrocarbons, more preferably, toluene. Preferably the carboxamide chain extending reagent will be an isocyanate, methyl ester such as β-alanine isocyanate, methyl ester, methyl glyconate isocyanate, and the like.

An alternative more preferred carboxamide chain extension step involves reaction of the compound of b) under the conditions, described below, for the conjugation step. Preferably, the compound to be chain extended is allowed to react with an activating reagent, described below, and the activated ester, with or without purification, is allowed to react with the carboxamide chain extending unit, preferably, an amino acid or poly(amino acid), more preferably, an unsubstituted amino acid such as glycine, alanine, valine, leucine, or isoleucine or poly(amino acids) made up of from about 2 to 12 residues thereof, still more preferably, the chain extending unit is composed of the 2 amino acid unit of gylcylglycine.

Any number of suitable chain extension steps can be performed in sequence in order to obtain various lengths of carboxamide extended chains.

The deprotection step of d) will be selected based upon the protecting group detailed above. The above cited and incorporated reference material describes the conditions and reagents for removal of the preferred protecting groups.

Typically, deprotection will involve aqueous hydrolysis at a pH of about 2–12, preferably, 3–11, more preferably, 4–10, in water at about 5–95° C., preferably, 10–40° C., more preferably, 20–25° C. Optional hydrolysis catalysts include acids or bases, preferably, HCl, $H_2SO_4$, HF, HBr, p-toluene sulfonic acid, NaOH, $Na_2CO_3$, $NaHCO_3$, $K_2CO_3$, or $KHCO_3$, more preferably, HCl or $K_2CO_3$. Optionally, an organic co-solvent can be used, typically, a protic solvent, preferably, an alcohol, more preferably, methanol.

An alternative preferred deprotection reaction will involve treatment with a source of fluoride ion such as HF, or an organic fluoride salt, preferably, a quaternary ammonium fluoride, more preferably, a tetraalkylammonium fluoride. The reaction is performed at the temperatures described above in an inert organic solvent, preferably, an ether, more preferably, diethyl ether or tetrahydrofuran.

The methods of carboxamide chain extension, as described above, are also useful for the activation and conjugation steps of e) and f).

Preferably, the activation and conjugation steps of e) and f) will be performed as is common in the art. For example, Maggio, E. T. "Enzyme-Immunoassay" (CRC Press, Boca Raton, Fla., 1980), Chapter 4, contains an assortment of such techniques; pages 81–86 of which are incorporated herein by reference.

More preferably, the cyclosporin-linking group conjugate will be activated by reaction with an activating reagent such as alkyl (of less than about 9 carbon atoms) chloroformate, e.g. isobutylchloroformate; dialkylcarbodiimide, e.g. dicyclohexylcarbodiimide; 1-ethyl-3-(3-dimethylamino propyl) carbodiimide (EDAC), 1-cyclohexyl-3-(2-morpholino-4-ethyl)carbodiimide methyl-p-toluenesulfonate (CMC), N-hydroxysuccinimide (NHS)/EDAC, N-hydroxysulfosuccinimide (sulfo-NHS)/EDAC, and the like, in an organic solvent such as DMF, and the like. The activation reaction is typically carried out at −10–100° C., preferably at 0–30° C., more preferably at 0–10° C., preferably, under an atmosphere of nitrogen, helium, argon, and the like. The activation reaction is carried out for from 1 minute to 10 days, preferably from 1 hour to 2 days, more preferably for 6–18 hours. After the activation reaction, the activated compound is added to a solution of the small organic molecule, or of the compound of molecular weight greater than 2,000 in an organic or aqueous/organic solvent such as DMF, or DMF/borate buffer, and the like. The addition can take place over a period of time or it may be performed in one portion. If the addition takes place over a period of time, it will typically require from 1 minute to 12 hours, preferably from 10 minutes to 8 hours, and more preferably from 30 minutes to 3 hours. After addition, the mixture is allowed to stir for from 1 minute to 3 days, preferably from 10 minutes to 1 day, more preferably from 1 to 18 hours.

The product is then optionally purified as may be required. The purification and characterization of poly (amino acid)-hapten conjugates has been described in detail Maggio, et. al; "enzyme-immunoassay" (CRC Press, Boca Raton, Fla., 1980), Chapter 4, pages 86–88 of which are incorporated herein by reference. For example, if the conjugate is a cyclosporin-immunogenic carrier conjugate, or a cyclosporin-enzyme conjugate, the purification can be by dialysis against aqueous/organic and aqueous solutions such as water/DMF or water, or by gel filtration chromatography on supports such as Sephadex, and the like.

Another aspect of the present invention includes antibodies prepared in response to an immunogen that is cyclosporin conjugated at an alanine nitrogen atom of the cyclic backbone of the cyclosporin to an immunogenic carrier. Furthermore, the present invention includes conjugates of such antibodies and a label.

Preferably, the antibodies are raised against cyclosporin A conjugated to an immunogenic carrier, optionally through a linking group of less than about 50 atoms other than hydrogen, preferably, less than about 35 atoms other than hydrogen, more preferably, less than about 20 atoms other than hydrogen having a chain of not more than about 35, preferably about 25, more preferably about 15 atoms in length, to an immunogenic carrier at the alanine nitrogen atoms of cyclosporin A amino acid residues no. 7 and/or 8.

An antibody is an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera from which the immunoglobulin can be separated by known techniques (polyclonal), by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies may include a complete immunoglobulin, or fragment thereof, which immunoglobulins include the various classes and isotypes, such as IgA, IgD, IgE, IgE, IgG1, IgG2a, IgG2b and IgG3, IgM, etc. Fragments thereof may include Fab, Fv and F(ab')2, Fab', and the like.

Monoclonal antibodies can be obtained by the process discussed by Milstein and Kohler and reported in *Nature* 1975, 256, 495–7. The details of this process are well known and will not be repeated here. However, basically it involves injecting a host, usually a mouse or other suitable animal, with an immunogen. Cells are then taken from the spleen of the animal. Alternatively, the host may be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones, each of which secretes a single antibody to the antigen.

The antibodies of the present invention are capable of specifically recognizing cyclosporin and closely related compounds containing the unmodified 9 carbon amino acid at position 1 (CsA numbering).

Conjugates of the antibodies of the present invention and a label can be prepared by methods already described above for the conjugation of poly(amino acids) to cyclosporin groups. The activation of the cyclosporin- linking group conjugate is performed as has been described. The conjugation of the activated compound to the antibody is performed as described above.

Preferably, the pH of a label conjugate reagent is optimized to balance, among any other considerations, the activity and stability of the label conjugate.

In one of its preferred embodiments, the present invention relates to cyclosporin—G6PDH conjugate reagents wherein the pH is 6–10, preferably 7–9, more preferably 7.5–8.5.

Preferably, the pH of antibody reagent is optimized to maximize the stability and precision of assay reagent components.

In one of its preferred embodiments, the present invention relates to cyclosporin antibody reagents wherein the pH is 4–7, preferably 5–6, more preferably 5.25–5.85.

Surface active additives, including bulking agents such as BLG or PEG; defoamers and surfactants such as tween-20, plurafax A38, triton X-100, pluronic 25R2, RSA, BSA, Mod-u-cyte, sol-u-pro, or the like; and other materials commonly used in the art can be added to both antibody and label conjugate reagents. Surface active additives can be added in order to maintain hydrophobic or compounds of low solubility in solution, stabilize assay reagent components, or optimize assay reagent activity.

Preferably, surface active additives will be added to antibody reagents in order to maintain cyclosporin in solution when the antibody reagent is added to the sample suspected of containing cyclosporin.

In one of its preferred embodiments, the present invention relates to cyclosporin antibody reagents containing one or more bulking agents, surfactants, and/or defoamers have been added.

Preferably, surface active additives will be added to label conjugates in order to maintain label conjugates in solution during storage and use.

In one of its preferred embodiments, the present invention relates to cyclosporin-G6PDH conjugate reagents containing one or more bulking agents, surfactants, and/or defoamers.

Anti-microbial agents can be added to assay reagents in order to extend the storage life of the reagents. Anti-microbial agents common in the art are useful. In one of its most preferred embodiments, the present invention relates to cyclosporin assay reagents containing anti-microbial agents.

Another aspect of the present invention relates to methods for measuring the amount of cyclosporin in samples suspected of containing cyclosporin. The antibodies and the label conjugates of the present invention can be utilized in the measurement of the amount of cyclosporin in a sample suspected of containing cyclosporin. The aassay can comprise the steps of optionally pretreating the sample followed by contacting the sample with antibodies for cyclosporin and measuring the amount of immune complexes of the antibodies and cyclosporin either directly or indirectly. The improvement provided in this aspect of the present invention is the utilization of the present antibodies as the antibodies for cyclosporin. The immune complexes are detected directly, for example, where the antibodies employed are conjugated to a label. The immune complex is detected indirectly by examining for the effect of immune complex formation in an assay medium on a signal producing system or by employing a labeled receptor that specifically binds to an antibody of the invention.

In another configuration of an assay for the determination of cyclosporin in an optionally pretreated sample suspected of containing cyclosporin, the sample is contacted with antibodies for cyclosporin and a label conjugate of this invention recognized by the antibodies. The method further includes measuring the amount of immune complexes of the label conjugate and the antibodies either directly or indirectly. Cyclosporin conjugated, optionally through a linking group of less than about 50, preferably 35, more preferably 20 atoms other than hydrogen having a chain of not more than about 35, preferably 25, more preferably 15 atoms in length, to a label may be employed as the label conjugate.

The assay of the invention has application to all immunoassays for cyclosporin. The assay can be performed either without separation (homogeneous) or with separation (heterogeneous) of any of the assay components or products. Exemplary of heterogeneous assays are enzyme linked immunoassays such as the enzyme linked immunosorbant assay (ELISA), see "Enzyme-Immunoassay" by Edward T. Maggio, CRC Press Incorporated, Boca Raton, Fla., 1980. Homogeneous immunoassays are exemplified by enzyme multiplied immunoassay techniques (e.g. see U.S. Pat. No. 3,817,837), immunofluorescence methods such as those disclosed in U.S. Pat. No. 3,993,345, enzyme channeling techniques such as those disclosed in U.S. Patent No. 4,233,402, and other enzyme immunoassays as discussed in Maggio, supra. The disclosures of the above patents are incorporated herein by reference in their entirety as to the description of the particular assay methods mentioned.

The sample to be analyzed can be pretreated in order to lyse cells which may be present, precipitate proteins which may be present, and/or solubilize cyclosporin which may be present. It is preferred that the samples to be analyzed by the method of the present invention be pretreated by contacting the sample with an organic solvent, preferably, an alcohol, more preferably, an alcohol having less than about 7 carbon atoms such as methanol.

The assay for the analyte will normally be carried out in an aqueous buffered medium at a moderate pH, generally that which provides optimum assay sensitivity.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members of any specific binding pairs and the pH optimum for other reagents of the assay such as members of the signal producing system.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50°, more usually from about 15° to 40° C.

The concentration of cyclosporin which may be assayed will generally vary from about $10^{-5}$ to $10^{-13}$ M, more usually from about $10^{-6}$ to $10^{-8}$ M. Considerations, such as whether the assay is qualitative, semiquantitative or quantitative (relative to the amount of cyclosporin present in the sample), the particular detection technique and the concentration of the cyclosporin will normally determine the concentrations of the various reagents.

While the concentrations of the various reagents in the assay medium will generally be determined by the concentration range of interest of cyclosporin, the final concentration of each of the reagents will normally be determined empirically to optimize the sensitivity of the assay over the range. That is, a variation in concentration of cyclosporin which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from about 30 seconds to 6 hours, more usually from about 1 minute to 1 hour.

In a homogeneous assay after all of the reagents have been combined either simultaneously or sequentially, the signal is determined. The signal is related to the amount of cyclosporin in the sample tested. For example, in the enzyme multiplied immunoassay technique, as described in U.S. Pat. No. 3,817,837 (1974) the disclosure of which is incorporated by reference, for the detection of cyclosporin, a sample suspected of containing cyclosporin is combined in an aqueous medium either simultaneously or sequentially with an antibody of the present invention and a cyclosporin enzyme conjugate of the present invention.

Generally, a substrate for the enzyme is added which results in the formation of a chromogenic or fluorogenic product upon enzyme catalyzed reaction. Preferably, the cyclosporin enzyme conjugate is cyclosporin A bound, optionally through a linking group of less than about 50 atoms other than hydrogen, preferably, less than about 35 atoms other than hydrogen, more preferably, less than about 20 atoms other than hydrogen having a chain of not more than about 35, preferably 25, more preferably 15 atoms in length, to an enzyme at the alanine nitrogen atom of cyclosporin amino acid residue no. 7. A particularly preferred enzyme is glucose-6-phosphate dehydrogenase. The cyclosporin in the sample and the cyclosporin-enzyme conjugate compete for sites on the antibody. The enzyme activity in the medium is then determined, usually by spectrophotometric means, and is compared to the enzyme activity determined when a calibrator or reference sample is tested in which a known amount of cyclosporin is present. Typically, the calibrator or reference sample is tested in a manner substantially the same as the sample suspected of containing cyclosporin. Generally, a comparison can be made of the result from an unknown sample with the results of assay runs on several standard samples. The standard samples will typically contain differing, but known, concentrations of the cyclosporin analyte to be determined. Preferably, the concentration ranges present in the standard samples will span the range of suspected analyte concentrations in the unknown samples.

Heterogeneous assays usually involve one or more separation steps. The heterogeneous assay can be competitive or non-competitive. In the competitive assay an antibody of the invention can be bound to a support, which is then contacted with a medium containing sample and cyclosporin conjugated to a detectable label such as an enzyme at an alanine nitrogen atom of the cyclic backbone of said cyclosporin. Cyclosporin in the sample competes with the conjugate for the sites on the antibody bound to the support. After separation of the support and the medium, the label activity of the support or the medium can be determined by conventional techniques and is related to the amount of cyclosporin in the sample.

In another competitive heterogeneous approach, an antibody of the invention is bound to a support. A medium is prepared containing a sample suspected of containing cyclosporin and cyclosporin conjugated to a residue of a small organic molecule (molecular weight less than 2,000) such as biotin at an alanine nitrogen atom of the cyclic backbone of said cyclosporin. Preferably, cyclosporin A is conjugated, optionally through a linking group of less than about 50 atoms other than hydrogen preferably, less than about 35 atoms other than hydrogen, more preferably, less than about 20 atoms other than hydrogen having a chain of not more than about 35, preferably 25, more preferably 15 atoms in length, through the alanine nitrogen atom of cyclosporin A amino acid residues no. 7 and/or 8. Cyclosporin and the conjugate compete for the antibody sites. After a period of time, the support is separated from the medium, washed, and contacted with a second medium containing a receptor or binding partner for the small organic molecule bound to a label such as an enzyme. If the small organic molecule is biotin, the support can be contacted with avidin bound to an enzyme. The support is separated from the second medium and enzyme activity of either the support or the second medium is determined by conventional methods. The enzyme activity is related to the amount of cyclosporin in the sample.

An example of a non-competitive approach is a sandwich assay involving two antibodies, one of which can be labeled and further one of which can be bound to a support or caused to become bound to a support.

In another aspect, agglutination can be utilized to determine the presence or amount of cyclosporin in a sample. Antibodies raised in response to cyclosporin conjugated at an alanine nitrogen atom of the cyclic backbone of said cyclosporin to an immunogenic carrier can be conjugated to particles. Preferably, the antibody is raised in response to cyclosporin A conjugated, optionally through a linking group of less than about 50 atoms other than hydrogen, preferably, less than about 35 atoms other than hydrogen, more preferably, less than about 20 atoms other than hydrogen having a chain of not more than about 35, preferably 25, more preferably 15 atoms in length, at the alanine nitrogen atom of cyclosporin A amino acid residues no. 7 and/or 8 to an immunogenic carrier. Preferred immunogenic carriers include KLH and BSA, more preferably, KLH.

Another conjugate that can be employed in the agglutination aspect is cyclosporin conjugated to a particle at an alanine nitrogen atom of the cyclic backbone of said cyclosporin. Preferably, cyclosporin A is conjugated, optionally through a linking group of less than about 50 atoms other than hydrogen, preferably, less than about 35 atoms other than hydrogen, more preferably, less than about 20 atoms other than hydrogen having a chain of not more than about 35, preferably 25, more preferably 15 atoms in length, at the alanine nitrogen atom of cyclosporin A amino residues no. 7 and/or 8.

In one approach in this agglutination aspect, a sample suspected of containing cyclosporin can be combined with an antibody-particle conjugate mentioned above. After an appropriate incubation, the extent of agglutination of the particles due to the presence of cyclosporin can be determined directly. On the other hand, the particles can be separated from the medium, washed, and combined with a cyclosporin conjugated to a particle in the manner described above. Agglutination can then be determined as a measure of the amount of cyclosporin in the sample. The above description exemplifies only two of many agglutination protocols that may be carried out utilizing the compounds of the invention.

Another aspect of the present invention relates to kits useful for conveniently performing the assay method of the invention for measuring the amount of cyclosporin in a sample suspected of containing cyclosporin. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises as one reagent an antibody raised in response to cyclosporin conjugated at an alanine nitrogen atom of the cyclic backbone of the cyclosporin to an immunogenic carrier. Preferably, the antibody raised in response to cyclosporin A is conjugated, optionally through a linking group of less than about 50 atoms other than hydrogen, preferably, less than about 35 atoms other than hydrogen, more preferably, less than about 20 atoms other than hydrogen having a chain of not more than about 35, preferably 25, more preferably 15 atoms in length, at the alanine nitrogen atom of cyclosporin A amino acid residues no. 7 and/or 8. Preferred immunogenic carriers include KLH and BSA, more preferably, KLH. This antibody can be labeled or unlabeled.

The kit may also include cyclosporin conjugated at an alanine nitrogen atom of the cyclic backbone of cyclosporin to a label. Preferably, cyclosporin A is conjugated, optionally through a linking group of less than about 50 atoms other than hydrogen, preferably, less than about 35 atoms other than hydrogen, more preferably, less than about 20 atoms other than hydrogen having a chain of not more than about 35, preferably 25, more preferably 15 atoms in length, at an alanine nitrogen atom of cyclosporin A amino acid residues no. 7 and/or 8. The kit can further include other packaged reagents for conducting an assay including members of the signal producing system, supports, ancillary reagents, and so forth.

A support, as described above in the definitions, is a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass, ceramics, metals, and the like.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

In another aspect, the present invention relates to atiocyclosporin conjugated, optionally through a linking group, to a label or to an immunogenic carrier.

Preferably the atiocyclosporin will be formed from a cyclosporin metabolite, more preferably, a cyclosporin A metabolite, still more preferably, cyclosporin A metabolite M1.

Preferably the linking group will be a bond or a group of from 1 to 60 atoms other than hydrogen having a chain of not more than about 30 atoms in length. More preferably, the linking group is a group of from 1 to 10 atoms other than hydrogen having a chain of not more than about 5 atoms in length.

The label and immunogenic carrier will be selected from the same groups as the labels and immunogenic carriers described above for cyclosporin conjugates. For enzyme assays the label will be an enzyme. Preferably a for a homogeneous enzyme immunoassay the label is a dehydrogenase, more preferably glucose-6-phosphate dehydrogenase. Preferably, the immunogenic carrier will be an antigenic poly(amino acid), more preferably keyhole limpet hemocyanin.

In one of its preferred embodiments the present invention relates to a composition of the formula:

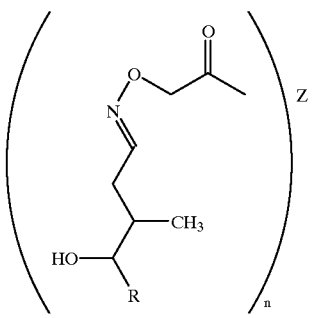

wherein R is of the formula:

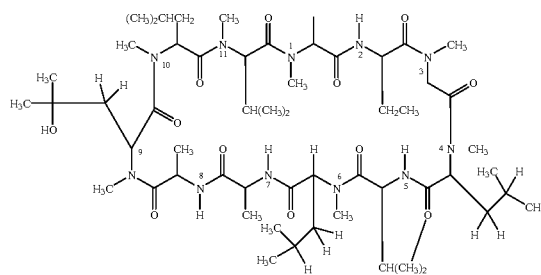

Z is an immunogenic carrier such as a protein, polysaccharide, lipoprotein, glycoprotein, and the like, and preferably is a polypeptide of molecular weight greater than 2000, more preferably Z is keyhole limpet hemocyanin or glucose-6-phosphate dehydrogenase and n is a number from 1 up to the molecular weight of Z divided by 5000.

In another aspect, the present invention relates to antibodies which are capable of recognizing cross-reactive material in an assay for cyclosporin and thereby preventing the material from interfering with the assay. Preferably, the assay will be one of the assays described above.

As described above, preferably, the interfering cross-reactive material will be a cyclosporin metabolite, more preferably, a cyclosporin A metabolite, still more preferably, cyclosporin A metabolite M1.

The antibodies of this aspect of the present invention will not interfere in the assay for measuring the amount of cyclosporin. Therefore, the antibodies will bind to the interfering cross-reactive material but will be substantially incapable of binding cyclosporin or cyclosporin-label conjugates under the assay conditions. Preferably, the antibodies will bind to cyclosporin A metabolites which still contain the undecapeptide ring, will not substantially bind to cyclosporin A, and will not substantially inhibit the enzymatic activity of cyclosporin-enzyme conjugates.

In one of its preferred embodiments the present invention relates to antibodies raised in response to a composition of the formula:

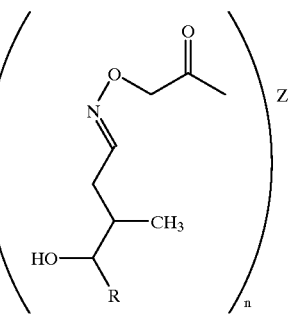

where R is of the formula:

Z is an immunogenic carrier such as a protein, polysaccharide, lipoprotein, glycoprotein, and the like, and preferably is a poly peptide of molecular weight greater than 2000, more preferably Z is keyhole limpet hemocyanin and n is a number from 1 up to the molecular weight of Z divided by 5000. These antibodies will be capable of binding to cyclosporin A metabolite M1, will not substantially recognize cyclosporin A, and will not substantially inhibit the enzymatic activity of cyclosporin A conjugated, optionally through a linking group, at the alanine nitrogen atom of cyclosporin A amino acid residue no. 7 to glucose-6-phosphate dehydrogenase.

The antibodies which are capable of recognizing interfering cross-reactive material can be prepared by the method, described above, for antibodies which recognize cyclosporin.

In another aspect, the present invention relates to methods of preparing atiocyclosporin conjugated, optionally through a linking group, to an immunogenic carrier or a label.

The method of preparing these conjugates includes the steps of:
(a) Oxidatively cleaving a cyclosporin metabolite at the olefinic side chain of amino acid residue no. 1;
(b) optionally extending the product of a) to form an atiocyclosporin—linking group conjugate,
(c) activating the product of b) for conjugation; and
(d) forming the conjugate by reacting the activated product of c) with a label or an immunogenic carrier.

Preferably, the oxidative cleavage reaction of step a) will cleave one or more bond or bonds connecting carbon atoms no. 6 and 7 of amino acid residue no. 1 of a cyclosporin metabolite. The cleavage reaction will produce a functional group on carbon atom no. 6. This functional group is any functional group such as hydroxy, keto, aldehyde, carboxylic acid, amino, imido, sulfide, disulfide, or the like, which can be used to either extend the sidechain to form an atiocyclosporin—linking group conjugate or to conjugate the atiocyclosporin directly through a bond to an immunogenic carrier or a label.

More preferably, the oxidative cleavage reaction will produce an atiocyclosporin carboxaldehyde. Two exemplary cleavage reactions of this type are ozonolysis and periodate cleavage. Periodate cleavage of 1,2-diols, which are in turn prepared by epoxidation/ring opening of double bonds, has been described in detail (Dryhurst, G. "Periodate oxidation of diol and other functional groups," (Pergamon Press, New York, 1970)). Ozonolysis of double bonds has also been described in detail ("Ozone Chemistry and Technology" (American Chemical Society, Washington, D.C. 1959); May D, F. R. "Oxidation of Organic Compounds" (American Chemical Society, Washington, D.C., 1967); Augustdine, R. L.; et al. "Oxidation" (Marcel Dekker, New York, 1971)).

Still more preferably, the oxidative cleavage reaction will be a solution phase ozonolysis followed by reductive workup. Preferred solvents for the reaction include haloalkanes such as dichloromethane. The temperature of the reaction is from −100° C. to 10° C., preferably from −78° C. to −50° C. The ozone is introduced into the reaction in a gas stream, preferably oxygen or air, more preferably, oxygen. The reaction is continued until the solution shows the characteristic blue color of ozone. Excess ozone is then removed from the solution, preferably by sweeping with an inert gas. The temperature of the reaction mixture is raised to less than 30° C., preferably less than 0° C., more preferably less than −10° C. A reducing agent is then added in order to produce the final aldehyde product. Preferably, the reducing agent is a dialkyl sulfide, more preferably, dimethyl sulfide.

The chain extending reaction b) may be any of the reactions, described above, for extending the linking groups of cyclosporin molecules. Preferably, the reaction of b) will be an aldehyde extending reaction. More preferably, the extension will be achieved by reacting an atiocyclosporin carboxaldehyde with an aminooxylakanoic acid.

Preferably, the aminooxyalkanoic acid will be aminooxyacetic acid, HCl Salt The reaction is carried out in an alkanol solvent, preferably a lower alkanol solvent, more preferably methanol. This reaction is carried out at between 0° C. and 100° C., preferably, 20° C. and 50° C., more preferably room temperature. This reaction is carried out under an inert atmosphere for between 1 min and 24 h, preferably, 10 min and 10 h, more preferably, 1 h and 2 h.

The activation reaction of c) is carried out as described above for the activation of cyclosporin—linking group conjugates preferably, the activation reaction involves treatment with sulfo-NHS.

The conjugation reaction of d) is carried out as described above for the conjugation reaction of cyclosporin—linking group conjugates preferably, the conjugation reaction involves treating an activated ester product of step c) with a poly(amino acid).

In one of its preferred embodiments, the present invention relates to a method of preparing compound (4) of scheme I. Step a) in scheme I is the cleavage of cyclosporin A metabolite M1 (compound (1), scheme I) with ozone followed by dimethyl sulfide workup. Step b) in scheme I is the chain extension of compound (2) by treatment with aminooxyacetic acid, HCl salt to form compound (3). Step c) in scheme I is activation of compound (3) with sulfo-NHS to form an activated ester. Step d) in scheme I is the coupling of the activated ester product of step c) with keyhole limpet hemocyanin or dehydrogenase to form the preferred compound (4).

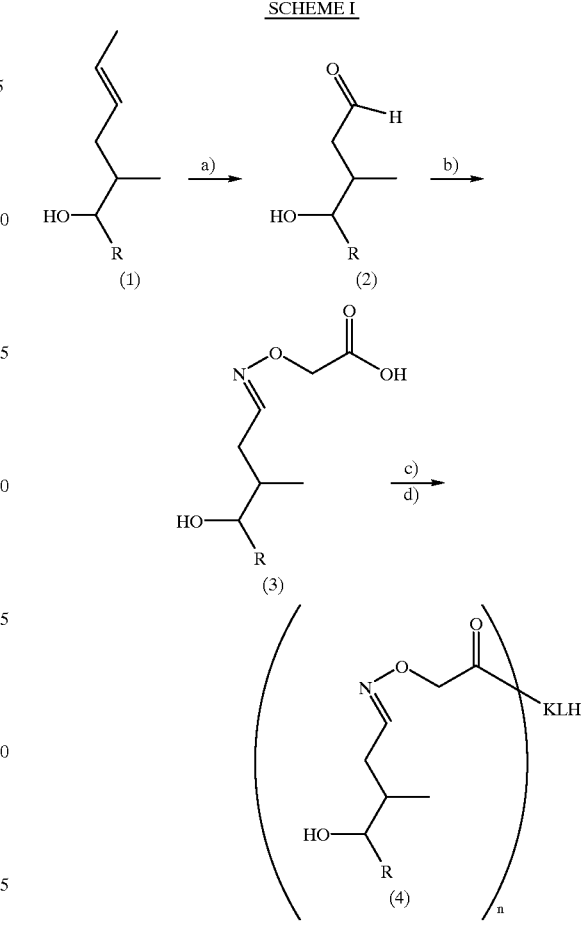

SCHEME I

KLH = keyhole limpet hemocyanin

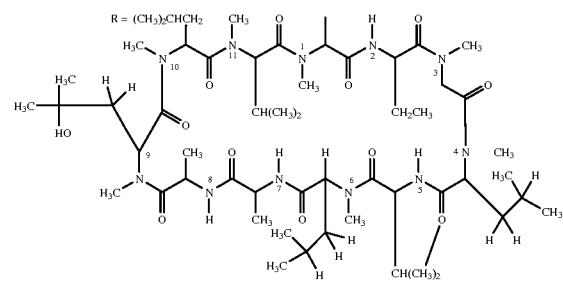

In another aspect, the present invention relates to a method of inactivating interfering cross-reactive material in an assay for measuring the amount of cyclosporin in a sample suspected of containing cyclosporin. Preferably, the assays is one of the assay for cyclosporin described above.

The inactivation method involves combining an assay medium containing the sample suspected of containing cyclosporin with an antibody capable of binding to the interfering cross-reactive material. Preferably, the assay medium is an assay medium described above.

The antibodies employed will not interfere in the assay for measuring the amount of cyclosporin. Preferably, the antibodies will not substantially bind cyclosporin under the assay conditions. Still more preferably, the antibodies will bind the interfering ross-reactive material, not substantially bind cyclosporin, and will not substantially bind a cyclosporin-label conjugate under the assay conditions.

In one of its preferred embodiments, the present invention involves combining antibodies which bind cyclosporin A metabolite M1, do not substantially bind cyclosporin A, and do not substantially inhibit (i.e. substantially recognize) cyclosporin A conjugated, optionally through a linking group; at the alanine nitrogen atoms of cyclosporin A amino acid residue no. 7, to glucose-6-phosphate dehydrogenase.

The amount of the antibody required to inactivate the interfering cross-reactive material depends on the amount of material present in the sample suspected of containing cyclosporin and upon the extent to which the material interferes with the assay. The more interfering material present and the greater its extent of cross-reactivity, the more antibody will be required sufficient antibody is added such that the cross-reaction is minimized without sacrificing assay performance.

The amount of M1 present in serum is reported to be as low as 9.6% and as high as 23% of total CsA (including metabolites) detected. The concentration of M1 is reported to be 30 to 90 ng/mL in a group of heart transplant patients and 226 to 544 ng/mL in a group of liver transplant patients. (see *Transplant Proceeding* 19988, VXX, 173–175 and 614–622) the extent of interference of metabolite M1 depends on the selectivity of the antibodies which bind cyclosporin. The lower the selectivity of the cyclosporin antibodies employed, the greater the extent of interference from M1.

In another aspect, the current invention relates to kits useful for conveniently performing the method of inactivating interfering cross-reactive material in an assay for cyclosporin. The preferred considerations for such kits have been described above and the kits will include an antibody in accordance with this aspect of the invention.

The following examples further describe the specific embodiments of the invention. These are typical illustrative examples and are intended to describe and not to limit the scope of the invention.

EXAMPLE 1

PROTECTED CYCLOSPORIN

To a stirred solution of cyclosporin A (1800 mg, 1.5 mmol) in dried pyridine (6 mL) and dried dichloromethane (6 mL) was added chlorotrimethylsilane dropwise at room temperature under an argon atmosphere. After the addition was complete, the mixture was stirred overnight. The mixture was then evaporated to dryness under vacuum, the solid residue was redissolved in dichloromethane, and purified on a silica gel column eluting with ethyl acetate/hexane (80:20) to give TMS protected cyclosporin A (Formula (XXV), TMS-CsA, 1700 mg, 89%); a white solid. M.P.: 152–156° C. I.R. (CHCl$_3$): 3650w, 3300s, 2950s, 2945s, 2850s, 1650s, 1415s, and 1400 cm$^1$. M.S.: m/e 1275 (M$^+$). The $^1$H and $^{13}$C NMR spectra were consistent with the assigned structure.

EXAMPLE 2

KEYHOLE LIMPET HEMOCYANIN CONJUGATE OF p-CARBOXYBENZYL CYCLOSPORIN

A. PROTECTED p-CARBOXYBENZYL CYCLOSPORIN

To a stirred solution of the product of Example 1 (900 mg, 0.71 mmol) in dried toluene (20 mL) was added 15-crown-5 ether (0.3 mL). Sodium hydride (350 mg, 50% suspension in mineral oil, washed with dried toluene) was then added at ice bath temperature under an argon atmosphere. The mixture was stirred and allowed to warm to room temperature over a period of 30 minutes. Methyl p-bromomethylbenzoate (400 mg, 2.5×0.71 mmol) was added, and the mixture was stirred for 24 hours at room temperature. Ethyl acetate (150 mL) was added, followed by slow and careful addition of water (50 mL), hydrochloric acid (1 N) was then added until the mixture was acidic (pH≅3.0). The organic layer was separated, washed with water (2×50 mL), brine (100 mL), and dried (MgSO$_4$). The solvent was removed under reduced pressure to give a pale foam (1.3 g) which was purified on a silica gel thin layer plate eluting with ethyl acetate/hexane (65:35; R$_f$≅0.6) to give a mixture (about 50:50) of TMS protected cyclosporin A bound, through the linking group of Formula (XIII), at the alanine nitrogen atom of cyclosporin A amino acid residues no. 7 and 8 to a methoxy group; a white solid (670 mg, 67%). M.S.: m/e 1,423 (M$^+$). The $^1$H and $^{13}$C NMR spectra were consistent with the assigned structure.

B. p-CARBOXYBENZYL CYCLOSPORIN

To a stirred solution of the product of Example 2A (280 mg, 0.197 mmol) in methanol (5 mL) was added water (dropwise, ≅1.5 mL or until the solution became slightly cloudy). Potassium carbonate (anhydrous, 230 mg) was added, the mixture was stirred for 12 hours and additional water was added dropwise until the solution became slightly cloudy. The mixture was stirred for another 12 hours at R.T. To the mixture was carefully added hydrochloric acid (1 N) until the solution became acidic (pH≅2.0). Water (50 mL) was added and the mixture was extracted with dichloromethane (3×50 mL). The organic extracts were combined, washed with brine (2×50 mL) and dried (MgSO$_4$). The solvent was removed under reduced pressure to give a crude product (270 mg) which was redissolved in dichloromethane (10 mL) and purified on a silica gel column eluting with ethylacetate until the starting material was removed and then with ethyl acetate/acetic acid (99.99:01) to give a mixture (about 50:50) of cyclosporin A bound, through the linking group of Formula (XIII), at the alanine nitrogen atom of cyclosporin A amino acid residues no. 7 and 8 to a hydroxy group (160 mg, 0.12 mmol, 63%); a white solid. M.P.: 171–177° C. I.R. (CHCl$_3$): 3700w, 3300w, 3000m, 2950s, 2920m, 2875m, and 1640 cm$^{-1}$. U.V.: (ethanol) 230 NM (ε=2.4×10$^4$). M.S.: m/e 1334 (M1, 24). Anal. Calcd. for C$_{70}$H$_{117}$N$_{11}$O$_{14}$: C, 62.90; H, 8.82; N, 11.06. Found: C, 62.10; H, 8.83; N, 10.80. The $^1$H and $^{13}$C NMR spectra were consistent with the assigned structure.

C. KEYHOLE LIMPET HEMOCYANIN IMMUNOGEN

To a stirred solution of the product of Example 2B (100 mg, 0.074 mmol) in dried DMF (1.3 mL) was added 1-ethyl-3-(3-dimethylamino propyl)carbodiimide (EDAC) (21 mg, 1.5×0.074 mmol) and N-hydroxysulfosuccinimide (sulfo-NHS) (25 mg, 1.5×0.074 mmol) at ice bath temperature under an argon atmosphere. The mixture was stirred overnight or until there was no starting material remaining by TLC analysis (ethylacetate/acetic acid, 99:1). This solution was added to a solution of keyhole limpet hemocyanin (KLH) (150 mg, 66% protein, 92% purity) in borate buffer (6 mL, 100 mM, pH≅9.1) and DMF (0.5 mL) over a period of 1.5 hours at ice bath temperature. After the addition was completed, the mixture was stirred in a 4° C. cold room (hereinafter referred to as "a cold room") overnight. The milky mixture was dialyzed against water/DMF (80:20), water/DMF (90:10), and finally water. The dialyzing bag content was then lyophilized to give a mixture (about 50:50) of cyclosporin A bound, through the linking group of Formula (XIII), at the alanine nitrogen atom of cyclosporin A amino acid residues no. 7 and 8 to a keyhole limpet hemocyanin (150 mg).

D. HAPTEN NUMBER DETERMINATION

To a solution of the product of Example 2C (0.59 mg/mL, 1 mL) in borate buffer (pH≅9.1, 100 mM) was added to a solution of 2,4,6-trinitrobenzene sulfonic acid (TNB) (0.1%, 1 mL) and the mixture was heated at 40° for 2 hours. After the mixture was cooled to R.T., a solution of sodium dodecyl sulfate (SDS) (10%, 1 mL) and hydrochloric acid (1 N, 1 mL) was added. A standard solution of KLH (purified, 1.09 mg/mL) in borate buffer (pH≅9.1, 100 mM) was prepared and treated with a TNBS solution (1 mL, 0.1%) at 40° C. for 2 hours. This standard solution was reacted with a SDS solution (10%, 1 mL) and hydrochloric acid (1 N, 1 mL). The absorbance of the sample and standard solutions at 340 nm were measured, and the hapten number calculated, according to the method of Habeeb, A. F. *Analytical Biochem*. 1966, 14, 328, and (incorporated herein by reference) was determined to be 1,100.

EXAMPLE 3

KEYHOLE LIMPET HEMOCYANIN CONJUGATE OF o-CARBOXYBENZYL CYCLOSPORIN

A. PROTECTED o-CARBOXYBENZYL CYCLOSPORIN

To a stirred suspension of sodium hydride (350 mg, 50% suspension in mineral oil, washed 3×10 mL with dried toluene) in dried toluene was added the product of Example 1 (900 mg, 0.71 mmol) at R.T. followed by addition of 15-crown-5 ether (0.35 mL). The mixture was stirred 30 minutes at R.T. under an argon atmosphere. Four portions of methyl o-bromomethylbenzoate were added (at time 0, 12 hrs, 24 hr, 36 hr; 508 mg was added at each time point for a total of 4×508 mg, 4×2 mmol). After the mixture was stirred for 36 hr at R.T., ethyl acetate (150 mL) was added, followed by careful addition of water (20 mL). The mixture was acidified with hydrochloric acid (1 N). The organic phase was separated, washed with water (3×30 mL), brine (50 mL), and dried ($MgSO_4$). The organic solvent was removed, the oily residue was redissolved in ethyl acetate and purified on a silica gel thin layer plate eluting with ethyl acetate/hexane (65:35, RF≅0.6) to give a mixture (about 50:50) of TMS protected cyclosporin A bound, through the linking group of Formula (XIV), at the alanine nitrogen atom of cyclosporin A amino acid residues no. 7 and 8 to a methoxy group (600 mg, 60%); a white solid. M.S.: m/e 1,423 ($M^+$). The $^1H$ and $^{13}C$ NMR spectra were consistent with the assigned structure.

B. o-CARBOXYBENZYL CYCLOSPORIN

To a stirred solution of the product of Example 3A (500 mg, 0.357 mmol) in methanol (10 mL) was added water (≅3.0 mL or until it became slightly cloudy). Potassium carbonate (anhydrous, 1000 mg) was added, (if the mixture remained cloudy, a few drops of methanol were added to obtain a clear solution). The mixture was stirred for 27 hours at R.T. under an argon atmosphere. Dichloromethane (150 mL) and water (50 mL) were added. The organic layer was separated, and the aqueous layer was extracted with dichloromethane (2×50 mL). The combined organic layers were washed with water/brine (1:1, 2×50 mL) and dried ($MgSO_4$). The solvent was evaporated to dryness to give the crude product (40 mg), which was purified on a silica gel column eluting with ethyl acetate until starting material and any non-acidic materials were removed, then it was eluted with a mixture of ethyl acetate/acetic acid (99.5:0.5) to give a mixture (about 50:50) of cyclosporin A bound, through the linking group of Formula (XIV), at the alanine nitrogen atom of cyclosporin A amino acid residues no. 7 and 8 to hydroxy group (350 mg, 0.26 mmol, 75%); a white solid. M.P.: 162–171° C. I.R. ($CHCl_3$): 3500w, 3450w, 3400m, 3300s, 2950m, 2850m, and 1620s, 1420m, 1400 and 1200b $cm^{-1}$. M.S.: m/e 1334 (M-1, 60). Anal. Calcd. for $C_{70}H_{117}N_{11}O_{14}$: C, 62.90; H, 8.82; N, 11.06. Found: C, 62.23; H, 8.48; N, 11.79. The $^1H$ and $^{13}C$ NMR spectra were consistent with the assigned structure.

C. KEYHOLE LIMPET HEMOCYANIN IMMUNOGEN

Using the product of Example 3B and the method of Example 2C, a mixture (about 50:50) of cyclosporin A bound, through the linking group of Formula (XIV), at the alanine nitrogen atom of cyclosporin A amino acid residues no. 7 and 8 to keyhole limpet hemocyanin was prepared in similar yield.

D. HAPTEN NUMBER DETERMINATION

Using the product of Example 3C and the method of Example 2D, a hapten number of 500 was determined.

EXAMPLE 4

BOVINE SERUM ALBUMIN CONJUGATE OF o-CARBOXYBENZYL CYCLOSPORIN

A. BOVINE SERUM ALBUMIN CYCLOSPORIN

Using the product of Example 3B and the method of Example 2C except that bovine serum albumin (BSA) was used in place of KLH, a mixture (about 50:50) of cyclosporin A bound, through the linking group of Formula (XIV), at the alanine nitrogen atom of cyclosporin A amino acid residues no. 7 and 8 to bovine serum albumin, (Cs-BSA) was obtained in similar yield.

B. HAPTEN NUMBER DETERMINATION

Using the method of Example 2D except that BSA was used in place of KLH, the hapten number of the Cs-BSA conjugate formed in Example 4A was found to be 55.

EXAMPLE 5

PROTECTED HYDROXYETHYL CYCLOSPORIN

To a stirred solution of the compound of Example 1 (1000 mg, 0.78 mmol) and 15-crown-5 ether (0.2 mL) in dried toluene (30 mL) was added sodium hydride (450 mg, 50% suspension in mineral oil, washed with dried toluene) at R.T. under an argon atmosphere. After 30 minutes, the reaction mixture was cooled to 4° C. and ethylene oxide (6 mL) was added via a syringe. The reaction flask was capped (sealed by stopper and parafilm) and stirred at R.T. for 24 hours. The reaction mixture was treated carefully with water (100 mL), acidified with hydrochloric acid (1 N) and dichloromethane (200 mL) added. The organic layer was separated, washed with water (100 mL), and dried ($MgSO_4$). The solvent was removed under reduced pressure to give the crude product as a white solid which was purified on a silica gel column eluting with ethylacetate to give TMS protected cyclosporin A bound, through the linking group of Formula (I), at the alanine nitrogen atom of cyclosporin A amino acid residue no. 7 to a hydroxy group; a white solid (350 mg, 34%). M.P.: 124–132° C. I.R. ($CHCl_3$): 3650w, 3400w, 3300m, 2950m, 1620s, 1460w, and 1400w and 1200b $cm^{-1}$. M.S.: m/e 1317 ($M^+$, 100), 1271 (M-$CH_2CH_2OH$, 10). The $^1H$ and $^{13}C$ NMR spectra were consistent with the assigned structure.

EXAMPLE 6

KEYHOLE LIMPET HEMOCYANIN CONJUGATE OF MONOCARBOXAMIDE EXTENDED HYDROXYETHYL CYCLOSPORIN

A. PROTECTED MONOCARBOXAMIDE EXTENDED HYDROXYETHYL CYCLOSPORIN

To a stirred solution of the product of Example 5 (300 mg, 0.23 mmol) and tri-n-butyltin ethoxide (154 mg, 0.4 mmol)

in dried toluene (2 mL) was added methyl glycinate isocyanate at R.T. under an argon atmosphere. The reaction mixture was stirred for 2 hrs. Ethyl acetate (50 mL) and water (50 mL) were added. The organic layer was separated, washed with brine/water (1: 1, 2×50 mL), and dried (MgSO$_4$). The solvent was removed under reduced pressure, and the crude product was purified on a silica gel column eluting with ethyl acetate to give TMS protected cyclosporin A bound, through the linking group of Formula (II), at the alanine nitrogen atom of cyclosporin A amino acid residue no. 7 to a methoxy group (280 mg, 0.20 mmol, 85%). M.S.: m/e 1433 (M+, 100). The $^1$H and $^{13}$C NMR spectra were consistent with the assigned structure.

B. MONOCARBOXAMIDE EXTENDED HYDROXYETHYL CYCLOSPORIN

To a st irred solution of the product of Example 6A (250 mg, 0.17 mmol) in methanol (10 mL) was added water until the mixture became slightly cloudy. Potassium carbonate (200 mg, anhydrous) was added, and the mixture was stirred overnight at R.T. under an argon atmosphere. The mixture was acidified with hydrochloric acid (1 N) and water (20 mL) was added. The mixture was extracted with dichloromethane (3×75 mL). The combined organic extracts were washed with brine (10 mL) and dried (MgSO$_4$). The solvent was removed under reduced pressure to give cyclosporin A bound, through the linking group of Formula (II), at the alanine nitrogen atom of cyclosporin A amino acid residue no. 7 to a hydroxy group; a white solid (220 mg, 0.16 mmol, 96%). M.P. 156–166° C. This material was about 95% pure but could be further purified on a silica gel column eluting with ethyl acetate/methanol/acetic acid (98:1.9:0.1, R.=0.15). I.R. (CHCl$_3$): 3650w, 3400w, 3300w, 2950m, 1700w, 1620s, 1460m, 1400m, and 1090w cm$^{-1}$. M.S.: m/e 1369 (M$^+$+Na, 60), 1347 (M+H, 50). The $^1$H and $^{13}$C NMR spectra were consistent with the assigned structure.

C. KEYHOLE LIMPET HEMOCYANIN CONJUGATE

To a stirred solution of the product of Example 6B (30 mg, 2.2×10$^{-2}$ mmol) in dried DMF (1 mL) was added EDAC (5.2 mg, 1.2×2.2×10$^{-2}$ mmol) and sulfo-NHS (5.8 mg, 1.2×2.2×10$^{-2}$ mmol) at 4° C. under an argon atmosphere. The mixture was then stirred in a cold room overnight. This solution was added to a KLH solution (100 mg, 66% protein, 92% purity) in borate buffer (pH≅9.1, 3.5 mL, 100 mM) and DMF (0.5 mL) over a period of 2 hrs. After the addition was complete, the mixture was stirred overnight in a cold room. The mixture was dialyzed against H$_2$O/DMF (75%:25%) and against water to give cyclosporin A bound, through the linking group of Formula (II), at the alanine nitrogen atom of cyclosporin A amino acid residue no. 7 to keyhole limpet hemocyanin (74 mg).

D. HAPTEN NUMBER DETERMINATION

Using the product of Example 6C and the method of Example 2D, a hapten number of 500 was determined.

EXAMPLE 7

KEYHOLE LIMPET HEMOCYANIN CONJUGATE OF TRICARBOXAMIDE EXTENDED HYDROXYETHYL CYCLOSPORIN

A. DICARBOXAMIDE-AMINO EXTENDED HYDROXYETHYL CYCLOSPORIN

To a stirred solution of the product of Example 6B (80 mg, 6×10$^{-2}$ mmol) in dried THF (1 mL) was added N-hydroxysuccinimide (NHS) (9.0 mg, 1.3×6×10$^{-2}$ mmol) and dicyclohexylcarbodiimide (DCC) (16.1 mg, 1.3×6×10$^{-2}$ mmol) at 4° C. under an argon atmosphere. The mixture was stirred overnight in a cold room and was added slowly to a solution of ethylene diamine (600 mg, 10 mmol) in THF (5 mL). The mixture was stirred for 4 hrs at R.T. and water (20 mL) was added. The mixture was extracted with dichloromethane (3×50 mL) and dried (Na$_2$SO$_4$). The solvent was removed under reduced pressure to give cyclosporin A bound, through the linking group of Formula (XI), at the alanine nitrogen atom of cyclosporin A amino acid residue no. 7 to an amino group (80 mg, 5.6×10$^{-2}$ mmol, 94%) which was used without further purification.

B. TRICARBOXAMIDE EXTENDED HYDROXYETHYL CYCLOSPORIN

To a stirred solution of the product of Example 7A (80 mg, 5.6×10$^{-2}$ mmol) in dried THF (1 mL) was added diglycolic anhydride (97%, 24 mg, 3×5.6×10$^{-2}$ mmol) and triethylamine (26 mg, 0.25 mmol) at R.T. under an argon atmosphere. The reaction was stirred overnight. Water (10 mL) and dichloromethane (50 mL) were added, and the mixture was acidified with hydrochloric acid (1 N). The organic phase was separated, and the aqueous phase was extracted with dichloromethane (2×25 mL). The combined organic layers were washed with brine (50 mL) and dried (MgSO$_4$). The solvent was removed under reduced pressure to give cyclosporin A bound, through the linking group of Formula (XII), at the alanine nitrogen atom of cyclosporin A amino acid residue no. 7 to a hydroxy group (70 mg, 83%); a glassy solid. M.S.: m/e 1505 (M+H, 30%). $^1$H NMR spectrum was consistent with the assigned structure.

C. KEYHOLE LIMPET HEMOCYANIN CONJUGATE

To a stirred solution of the product of Example 7B (60 mg, 4×10$^{-2}$ mmol) in DMF (1 mL) was added NHS (5.5 mg, 1.2×4×10$^{-2}$ mmol), DCC (9.8 mg, 1.2×4×10$^{-2}$ mmol) at 4° C. under an argon atmosphere. The mixture was stirred overnight. The solution was added to a solution of KLH (120 mg, 66% protein, 92% pure) in phosphate buffer (6 mL, pH≅8.3, 100 mM) and DMF (0.8 mL) over a 3 hr period at 4° C. After addition was complete, the mixture was stirred overnight in a cold room. The mixture was dialyzed against H$_2$O/DMF (90:10) and water. The conjugate was then lyophilized to give cyclosporin A bound, through the linking group of Formula (XII), at the alanine nitrogen atom of cyclosporin A amino acid residue no. 7 to keyhole limpet hemocyanin (120 mg).

D. HAPTEN NUMBER DETERMINATION

Using the product of Example 7C and the method of Example 2D, a hapten number of 700 was determined.

EXAMPLE 8

MONOCARBOXAMIDE EXTENDED HYDROXYETHYL CYCLOSPORIN HOMOLOG

A. PROTECTED MONOCARBOXAMIDE EXTENDED HYDROXYETHYL CYCLOSPORIN HOMOLOG

To a stirred solution of the product of Example 5 (60 mg, 4.5×10$^{-2}$ mmol) and tri-n-butyltin ethoxide (30 mg, 8.9×10$^{-2}$ mmol) in dried toluene (1 mL) was added β-alanine isocyanate methyl ester. The mixture was stirred for 2 hrs. Ethyl acetate (50 mL) and water (50 mL) were added, the organic layer was separated and washed with brine/water (1:1, 2×50 mL) and dried (MgSO$_4$). The organic phase was removed under reduced pressure, and the foamy solid was purified on a silica gel column eluting with ethyl acetate to give TMS protected cyclosporin A bound, through the linking group of Formula (IX), at the alanine nitrogen atom of cyclosporin A amino acid residue no. 7 to a methoxy group (59 mg, 4.1×10$^{-2}$ mmol, 91%).

B. MONOCARBOXAMIDE EXTENDED HYDROXYETHYL CYCLOSPORIN HOMOLOG

To a stirred solution of the product of Example 8A in methanol (1 mL) was added water and potassium carbonate (30 mg, anhydrous) and the mixture was stirred for 20 hrs. The mixture was acidified with hydrochloric acid (1 N), water (20 mL) was added, the mixture was extracted with dichloromethane (2×20 mL), and dried (MgSO$_4$). This material was purified on a silica gel column eluting with ethylacetate/methanol/acetic acid (98:2:0.1) to give cyclosporin A bound, through the linking group of Formula (IX), at the alanine nitrogen atom of cyclosporin A amino acid residue no. 7 to a hydroxy group (25 mg, 90%). M.S.: m/e 1318 (M+H, 100).

EXAMPLE 9

MONOCARBOXAMIDE EXTENDED HYDROXYETHYL CYCLOSPORIN THIO ANALOG

A. PROTECTED MONOCARBOXAMIDE EXTENDED HYDROXYETHYL CYCLOSPORIN THIO ANALOG

To a stirred solution of the product of Example 5 (60 mg, 4.5×10$^{-2}$ mmol) and tri-n-butyltin ethoxide (70 mg, 0.2 mmol) in dried toluene (1 mL) was added acetic acid isothiocyanate methyl ester (90 mg). The mixture was stirred for 2 hrs. Ethyl acetate (50 mL) and water (50 mL) were added. The organic layer was separated and washed with brine/water (1:1, 2×50 mL) and dried (MgSO$_4$). The organic phase was removed under reduced pressure, and the foamy solid was purified on a silica gel column eluting with ethyl acetate to give TMS protected cyclosporin A bound, through the linking group of Formula (X), at the alanine nitrogen atom of cyclosporin A amino acid residue no. 7 to a methoxy group (55 mg, 3.8×10$^{-2}$ mmol).

B. MONOCARBOXAMIDE EXTENDED HYDROXYETHYL CYCLOSPORIN THIO ANALOG

To a stirred solution of the product of Example 9A (55 mg, 3.4×10$^{-2}$ mmol) in methanol (10 mL) was added water and potassium carbonate (30 mg, anhydrous) and the mixture was stirred for 20 hrs. The mixture was acidified with hydrochloric acid (1N), water (20 mL) was added, the mixture was extracted with dichloromethane (2×20 mL), and dried (MgSO$_4$). This material was purified on a silica gel column eluting with ethylacetate/methanol/acetic acid (98:2:0.1) to give cyclosporin A bound, through the linking group of Formula (X), at the alanine nitrogen atom of cyclosporin A amino acid residue no. 7 to a hydroxy group (50 mg, 3.4×10$^{-2}$ mmol, 89%). M.S.: m/e 1496 (70%), 1363 (80%).

EXAMPLE 10

MONOCARBOXAMIDE EXTENDED HYDROXYETHYL CYCLOSPORIN ALKYL ANALOG

A. PROTECTED MONOCARBOXAMIDE EXTENDED HYDROXYETHYL CYCLOSPORIN ALKYL ANALOG

Using the product of Example 5 and the method of Example 8A (except that α-alanine isocyanate methyl ester was used in place of β-alanine isocyanate methyl ester), TMS protected cyclosporin A bound, through the linking group of Formula (VI), at the alanine nitrogen atom of cyclosporin A amino acid residue no. 7 to a methoxy group, was prepared in similar yield.

B. MONOCARBOXAMIDE EXTENDED HYDROXYETHYL CYCLOSPORIN ALKYL ANALOG

Using the product of Example 10A and the method of Example 8B, cyclosporin A bound, through the linking group of Formula (VI), at the alanine nitrogen atom of cyclosporin A amino acid residue no. 7 to a hydroxy group, was prepared in 90% yield. M.S.: m/e 1399 (M+K, 100%), 1383 (M+Na, 70%), 1362 (M+H, 30%).

EXAMPLE 11

MONOCARBOXAMIDE EXTENDED HYDROXYETHYL CYCLOSPORIN AROMATIC ANALOG

A. PROTECTED MONOCARBOXAMIDE EXTENDED HYDROXYETHYL CYCLOSPORIN AROMATIC ANALOG

Using the product of Example 5 and the method of Example 8A (except that α-phenyl α-alanine isocyanate, methyl ester was used in place of α-alanine isocyanate, methyl ester), TMS protected cyclosporin A bound, through the linking group of Formula (V), at the alanine nitrogen atom of cyclosporin A amino acid residue no. 7 to a methoxy group, was prepared in similar yield.

B. MONOCARBOXAMIDE EXTENDED HYDROXYETHYL CYCLOSPORIN AROMATIC ANALOG

Using the product of Example 10A and the method of Example 8B, TMS protected cyclosporin A bound, through the linking group of Formula (V), at the alanine nitrogen atom of cyclosporin A amino acid residue no. 7 to a hydroxy group, was prepared in similar yield. M.S.: m/e 1422 (M−H, 30%).

EXAMPLE 12

CARBOXYMETHYL EXTENDED HYDROXYETHYL CYCLOSPORIN

A. PROTECTED CARBOXYMETHYL EXTENDED HYDROXYETHYL CYCLOSPORIN

To a stirred solution of the product of Example 5 (130 mg, 9.8×10$^{-2}$ mmol) in dried THF (1.5 mL) was added sodium hydride (20 mg, 50% suspension in mineral oil, washed in dried THF) and 15-crown-5 ether (≅20 mg) at R.T. under an atmosphere of argon. The mixture was stirred for 1 hr and α-bromoacetic acid, methyl ester (80 mg) in dried THF (0.5 mL) was added. The reaction was stirred for an additional 2 hrs, another portion of α-bromoacetic acid, methyl ester (80 mg) was added, and the reaction was stirred for 2 hrs. Ethyl acetate (50 mL) and water (20 mL) were added, and the mixture was acidified with hydrochloric acid (1 N) (pH≅3.0). The organic phase was separated, washed with water (2×50 mL) and dried (MgSO$_4$). The solvent was removed under reduced pressure, and the residue was purified on a silica gel thin layer plate eluting with ethyl acetate to give TMS protected cyclosporin A bound, through the linking group of Formula (VII), at the alanine nitrogen atom of cyclosporin A amino acid residue no. 7 to a methoxy group (80 mg, 60%); a white solid. M.S.: m/e 1358 (M−H, 100). The $^1$H NMR spectrum was consistent with the assigned structure.

B. CARBOXYMETHYL EXTENDED HYDROXYETHYL CYCLOSPORIN

To a stirred solution of the product of Example 12A (79 mg, 5.8×10$^{-2}$ mmol) in methanol (4 mL) was added water until the mixture became cloudy (≅1.5 mL). Potassium carbonate (anhydrous, 40 mg) was added, and the mixture was stirred for 20 hrs. The mixture was acidified with hydrochloric acid (1 N), and water (20 mL) was added, the mixture was extracted with dichloromethane (2×20 mL), and dried (MgSO$_4$). The crude product was purified on a silica gel column eluting with ethylacetate/methanol/acetic acid (98:2:0.1) to give cyclosporin A bound, through the linking group of Formula (VII), at the alanine nitrogen atom of cyclosporin A amino acid residue no. 7 to a hydroxy group (65 mg, 80%); a white solid. M.S.: m/e 1326 (M+Na), 1304 (M+H). The $^1$H NMR spectrum was consistent with the assigned structure.

EXAMPLE 13

KEYHOLE LIMPET HEMOCYANIN CONJUGATE OF DICARBOXAMIDE EXTENDED p-CARBOXYBENZYL CYCLOSPORIN

A. DICARBOXAMIDE EXTENDED p-CARBOXYBENZYL CYCLOSPORIN

To a stirred solution of the product of Example 2B (60 mg) in DMF (0.69 mL) was added N-hydroxysulfosuccinimide (sulfo-NHS, 12.8 mg) and (1-ethyl-3(3-dimethylamino propyl)carbodiimide (EDAC, 13.9 mg) at 40° C. under an argon atmosphere. The reaction mixture was allowed to stir overnight at 4° C. Complete formation of the sulfo-NHS ester was observed by TLC (silica gel, eluant 0.15:2:8, acetic acid/methanol/dichloromethane) after 18 hours. The resulting sulfo-NHS ester was added slowly to a solution of glycylglycine (12.1 mg) in a mixture of borate buffer (1 mL, pH 9, 0.05 M) and DMF (2 mL), with the adjustment of pH in the range of 8.5 to 9 over a period of 30 minutes at 4° C. The light yellow solution was allowed to stir at 4° C. for an additional 30 minutes and at room temperature for 2 hours. To the resulting product was added 1N HCl (until the mixture was pH 4) and the precipitate was collected and dried under vacuum to yield a white product (49 mg). The filtrate was extracted with ethyl acetate, the organic extracts were dried ($Na_2SO_4$), and the solvent was evaporated to yield a second quantity of product. The combined products were purified by preparative layer chromatography (silica gel, eluant 3:40:160, acetic acid/methanol/dichloromethane) to yield a mixture (about 50:50) of cyclosporin A bound, through the linking group of Formula (XIX), at the alanine nitrogen atom of cyclosporin A amino acid residue no. 7 and 8 to a hydroxy group, (29 mg). M.S.: m/e 1450 (M+H), 1488 (M+K).

B. KEYHOLE LIMPET HEMOCYANIN CONJUGATE

To the product of Example 13A (20 mg) in DMF (300 µL) was added EDAC (3.1 mg) and N-hydroxysulfosuccinimide (3.58 mg) in DMF (300 µL). The reaction mixture was allowed to stir overnight at 4° C. Incomplete formation of sulfo-NHS ester was observed by TLC (silica gel, eluant 3:40:160, acetic acid/methanol/dichloromethane). Additional EDAC (3.1 mg) and N-hydroxysulfosuccinimide (3.58 mg) were added. The reaction mixture was allowed to stir at room temperature for 4 hours. Complete reaction was observed by TLC (silica gel, eluant 3:40:160, acetic acid/methanol/dichloromethane). To a solution of KLH (40 mg) in a mixture of borate buffer (3.0 mL, pH 9, 0.05M) and DMF (0.7 mL) was added the sulfo-NHS ester reaction mixture, prepared above, over a period of 4 hours at room temperature with constant pH adjustment to pH 8.5. An additional quantity of DMF (0.25 mL) was added during the 4 hour period. The resulting mixture was stirred at 4° C. overnight. The cloudy mixture was dialyzed against 10% DMF/water (pH 8 with $NH_4OH$, 3×4 L) and water (pH 8 with $NH_4OH$, 5×4 L). The resulting product was lyophilized to yield cyclosporin A bound, through the linking group of Formula (XIX), at the alanine nitrogen atom of cyclosporin A amino acid residue no. 7 and 8 to keyhole limpet hemocyanin (32 mg).

C. HAPTEN NUMBER DETERMINATION

Using the product of Example 13B and the method of Example 2D, a hapten number of 948 was determined.

EXAMPLE 14

CYCLOSPORIN, GLUCOSE-6-PHOSPHATE DEHYDROGENASE CONJUGATES

A. ACTIVATION OF CYCLOSPORIN HAPTEN

Into a flame-dried flask was placed 35 mg of cyclosporin hapten, in particular, the product of Example 6B, 6.2 mg of Sulfo-NHS, 5.5 mg of EDAC, and 0.35 ml of DMF. The mixture was stirred overnight at 4° C.

B. CONJUGATION TO GLUCOSE-6-PHOSPHATE DEHYDROGENASE

The product of Example 14A was added portionwise to a solution of glucose-6-phosphate dehydrogenase (G6PDH, 0.055m in sodium carbonate buffer) glucose-6-phosphate (G6P, 4.5 mg/mg G6PDH), and NADH (9 mg/mg G6PDH) in a pH 8.8 sodium carbonate buffer/DMF (0.2 mL/mL. of buffer) at ice bath temperature. The reaction was monitored and stopped at 29–35% inhibition of enzyme activity in the presence of anti-CsA antibody relative to enzyme activity in the absence of anti-CsA antibody.

C. CONJUGATE ISOLATION

The conjugate of this Example 14B cyclosporin A bound, through the linking group of Formula (II), at the alanine nitrogen atom of cyclosporin A amino acid residue no. 7 to glucose-6-phosphate dehydrogenase was isolated by chromatographic separation on G100 sephadex using 0.055 M Tris-HCl (pH 8.0) containing 0.05% sodium azide and 0.005% Thimerosal. Hapten numbers of less than about 5–10 were obtained at inactivations of less than about 35%.

The products of Examples 2B, 3B, 7B, 8B, 9B, 10B, 11B or 12B, were also converted to the corresponding G6PDH conjugates by this method of Example 14.

EXAMPLE 15

PREPARATION CYCLOSPORIN OF MONOCLONAL ANTIBODIES

A. GENERAL METHODS

The standard hybridoma procedures used have been described in detail (Kohler, G.; Milstein, C. Nature 1975, 256, 495–7; Hurrell, J. G. R. "Monoclonal Hybridoma Antibodies: Techniques and Applications", CRC Press, 1982, Boca Raton, Fla. 33431).

B. IMMUNIZATION

BALB/C mice were immunized with 50 to 200 µg of immunogen (particularly the KLH conjugate of Example 13B) in Complete Freunds Adjuvant (CFA) by intraperitoneal (IP), or subcutaneous (SC) injection. Boosting with immunogen (incomplete Freund's adjuvant (IFA), IP, or SC) was performed monthly. A final IP, SC, or intravenous (IV) injection of 100–500 µg in saline was performed prior to fusion.

C. IMMUNIZATION MONITORING

A serum antibody forward ELISA test was used to monitor mice after about 2 to 3 immunizations. Serum antibody titers were two fold serially diluted prior to assay.

Microtiter EIA plates (Costar #3590) were coated with 50 µL/well of the G6PDH enzyme-conjugate labeled with the same hapten as the immunogen, diluted 1:100 in phosphate buffered saline (PBS, 0.01 M sodium phosphate, 0.15 M sodium chloride, and 0.02% sodium azide, pH 7.2), incubated at 37° C. for 1 hour, and then 300 µL/well of 1% normal sheep serum (NSS) in PBS was added to block nonspecific binding. After a 30 minute wait, the contents of the plates were dumped out. Serum, serially diluted, was added, 50 µL/well and incubated 30 minutes at 37° C. The plates were washed 3 times with ELISA wash buffer (0.05t Tween-20, [Fisher Scientific Co. #CS-279-3], in PBS, pH 7.2). Goat anti-mouse sera labeled with alkaline phosphatase (IgG+IgM+light chain specific, Tago #6543), diluted 1:1000 in PBS, was added to the plates, 50 µL/well, and allowed to incubate for an additional 30 minutes at 37° C. The plates were washed as before, and then 100 µL/well of substrate (15 mg of p-nitrophenyl phosphate, disodium [PNPP, Sigma #S104–105], per 25 mL of 10% diethanolamine [Eastman-Kodak #1598], pH 9.8, containing 0.5 mM $MgCl_2$ [Mallinckrodt #5958]) was added. The plates were allowed to sit on a shaker at room temperature for about 30 minutes or until there was visible color development. The plates were then read on a Titertek Multiscan at 405 nm. OD readings were plotted against the dilution of the serum sample. Serum antibody titer was defined as the dilution at which there is a 70% reduction in OD from the highest OD of the titration curve.

D. CELL FUSION

Spleen cells were harvested from the immunized mice and fused with P3 X63-AG8.653 myeloma cells using PEG. The cells were resuspended in HAT supplemented media and distributed into 96-well microtiter plates. Four days later cells were fed by replacing half the HAT supplemented media.

E. HYBRIDOMA SCREENING

About 1 week after cell fusion, hybridomas were screened for specific antibodies. A reverse ELISA assay was used to screen for antibody production.

Microtiter EIA plates were coated with 50 µL/well with rabbit anti-mouse specific antibody to IgG+IgA+IgM, H+L chains (Zymed #61-6400 SY), diluted 1:100 in PBS, pH 7.2, and stored for up to a week at 4° C. until needed. The plates were filled with 300 µL/well of 1% NSS/PBS to block unspecific binding and allowed to sit for 30 minutes and then dumped out. Spent media, 50 µL/well, were then added and incubated for 30 to 60 minutes at 37° C. The plates were then washed 3 times. G6PDH enzyme labeled with the same hapten as the immunogen, was diluted 1:100 to 1:700 in PBS, 50 µL/well was added, and then incubated for 30 to 60 minutes at 37° C. Plates were again washed as before, and 100 µL/well of substrate (0.053 M trizma base [Sigma #T1503], 0.02 M NAD, 0.033 M G-6-P, 0.025% NaN [sodium azide, J. T. Baker #7-V015], pH adjusted to 6.2 with HCl, 0.63 mM p-iodonitrotetrazolium violet [INT, Sigma #I8377], 1% NSS, and 60 units/mL diaphorase [Sigma #2381]) was finally added. Plates were incubated for about one hour at room temperature on a shaker and read on a Titertek Multiscan at 492 nm. Wells with readings at least two times higher than the background were considered ELISA+.

F. ANTIBODY PRODUCTION IN ASCITES

To scale up monoclonal antibody production in ascites, mice were primed by an IP injection of IFA to induce tumor growth, 0.3 to 0.5 mL/mouse, 2 to 7 days prior to passage of cells. Cells were grown up in log phase in a T-75 flask, about $18 \times 10^6$ cells, centrifuged, and then resuspended in 2 mL of S-DMEM. Each mouse received a 0.5 mL IP injection of approximately $4–5 \times 10^6$ cells. An ascites tumor usually developed within a week or two. The ascites fluid containing a high concentration of antibody was then drained using an 18-gauge needle. The fluid was allowed to clot at room temperature and then centrifuged at 1500 rpm for 30 minutes. The antibody containing fluid was poured off and stored frozen at −20° C.

Antibodies were also raised against the products of Examples 2C, 3C, 6C, 7C and 4A by the method of this Example 15.

EXAMPLE 16

SELECTION OF ANTIBODIES AND ENZYME CONJUGATES

A. GENERAL FACTORS

The selection of optimum monoclonal antibodies and enzyme conjugates for use in the EMIT® assay for cyclosporin is dependent on a number interrelated factors. Primarily, the antibody must recognize and affect the activity of the enzyme conjugate. Because glucose-6-phosphate dehydrogenase (G6PDH) is a preferred enzyme, the antibody will be selected based on its ability to inhibit the activity of a glucose-6-phosphate conjugate. Additionally, the antibody will be selected based on its ability to recognize cyclosporins of interest. For example, if an assay capable of detecting cyclosporin A and not its metabolites is desired, then an antibody with this specificity will be selected. Alternatively if an assay capable of detecting cyclosporin A and its principle metabolites is desired, then an antibody with this specificity will be selected.

Other selection factors include the stability, ease of preparation, and solubilities of the antibodies and enzyme conjugates.

Details of the assay to be performed also affect the selection of antibodies and enzyme conjugates. For example, the sample could be whole blood, serum, urine, and the like. The assay diluent, stabilizing additives, buffer components, defoamers, and pretreatment could affect the selection of antibodies and enzyme conjugates.

The above described factors are general and interrelated. The selection of optimum antibodies and enzyme conjugates will involve careful balancing of some of the factors described above as well as other factors of importance in the specific assay of interest.

B. ENZYME CONJUGATE SCREENING

Cyclosporin A, Glucose-6-phosphate dehydrogenase conjugates prepared in Example 14 were screened for percent inhibition when treated with two of the antibodies (clones 5E10 and 2G4) of Example 15. Key selection factors included maximizing conjugate inhibitability and stability.

TABLE 1

| Cyclosporin-G6PDH Conjugate Screening | | | | |
|---|---|---|---|---|
| Linking Group | H/E Ratio[a] | % D[b] | % I[c] (5E10) | % I[c] (2G4) |
| I | 392 | 50 | 3.7 | |
| II | 39 | 26 | 4.0 | |
| | 63 | 37 | 60.5 | |
| | 93 | 56 | 63.2 | |
| III | 33 | 56 | 3.5 | |
| | 65 | 79 | 6.7 | |
| V | 73 | 62 | 10.7 | 6.5 |
| VI | 70 | 45 | | 37.3 |
| VII | | 31 | 53.0 | 41.0 |
| | | 52 | 64.4 | 52.5 |
| VIII | 217 | 47 | 11.4 | |
| IX | | 36 | | 44.5 |
| XIII | 380 | 37 | 5.9 | |
| XIV | 202 | 27 | 13.0 | |
| | 347 | 47 | 25.0 | |
| | 551 | 64 | 29.0 | |
| XV | 319 | 56 | 18.5 | |

[a]Final molar ratio of hapten to enzyme in the conjugation reaction mixture
[b]Percent deactivation
[c]Percent enzyme inhibition

C. ANTIBODY SCREENING

Antibodies of Example 15 were screened for percent inhibition against Glucose-6-Phosphate conjugates of Example 14. Key selection factors included maximizing inhibition of enzyme conjugates and reduction in inhibition by addition of CsA.

TABLE 2

Cyclosporin Antibody Screening Percent Inhibition

| Clone | G6PDH Conjugate Linking Group | | | |
|---|---|---|---|---|
|  | II | XIII | XIV | V |
| KLH Immunogen Linking Group XIII | | | | |
| 3E3 | 35 | 4 | 33 | 18 |
| 16K9 | 20 | 3 | 20 | 10 |
| 13A11 | 26 | 1 | 22 | 10 |
| 4B10 | 47 | 7 | 39 | 21 |
| 6F11 | 25 | 2 | 27 | 15 |
| 2F9 | 12 | 5 | 13 | 5 |
| 11C6 | 16 | 3 | 18 | 11 |
| 2E3 | 13 | 3 | 16 | 9 |
| 12H5 | 30 | 1 | 20 | 9 |
| 5F2 | 13 | 1 | 13 | 6 |
| KLH Immunogen Linking Group XIV | | | | |
| 4A10 | 19 | 6 | 18 | 10 |
| 5E6 | 22 | 3 | 23 | 10 |
| 6H1 | 11 | 3 | 18.4 | 11.3 |
| 6B10 | 27 | 2 | 18 | 8 |
| 2G5 | 45 |  | 2 | 1 |
| 4C7 |  | 2 | 4.5 | 3 |

TABLE 3

Cyclosporin Antibody Screening Percent Inhibition Against G6PDH Conjugate Linking Group II

| Clone | % I |
|---|---|
| KLH Immunogen, Linking Group XIII | |
| 7D4 | 45 |
| 2G5 | 45 |
| 7G10 | 17 |
| 5G5 | 3 |
| 8A1 | 1 |
| 5E10 | 55 |
| 15B8 | 18 |
| 14A9 | 2 |
| 3C8 | 25 |
| 3B4 | 17 |
| 9H8 | 27 |
| 10C6 | 27 |
| 9H7 | 46 |
| 10B6 | 24 |
| 8F2 | 12 |
| 9E7 | 22 |
| 1G1 | 19 |
| 10H3 | 14 |
| 10H9 | 23 |
| 3B7 | 18 |
| 2D8 | 34 |
| 9A10 | 22 |
| 6G11 | 38 |
| KLH Immunogen, Linking Group XIV | |
| 5F7 | 25 |
| 3A8 | 18 |
| 3H2 | 9 |
| 2G2 | 22 |
| 5E12 | 31 |
| 3G6 | 24 |
| 2A3 | 52 |
| 10E6 | 47 |
| 4D7 | 59 |
| 5F5 | 46 |

TABLE 3-continued

Cyclosporin Antibody Screening Percent Inhibition Against G6PDH Conjugate Linking Group II

| Clone | % I |
|---|---|
| 7G10 | 57 |
| 7H4 | 46 |
| 19C5 | 36 |
| 4A10 | 20 |
| 5E6 | 22 |
| 6H1 | 11 |
| 6B10 | 27 |
| 6F12 | 15 |
| 8D9 | 2 |
| KLH Immunogen, Linking Group XIX | |
| 2G4 | 42 |
| 7D9 | 4 |
| 2E3 | 13 |
| 3E3 | 35 |
| 16K9 | 20 |
| 13A11 | 26 |
| 4B10 | 47 |
| 6F11 | 25 |
| 2F9 | 12 |
| 11C6 | 16 |
| 12H5 | 30 |
| 5F2 | 13 |
| 18H6 | 30 |
| 4E9 | 46 |
| 12G10 | 53 |
| 3A3 | 47 |
| 9D10 | 19 |
| 6E10 | 28 |

D. ANTIBODY CROSS-REACTIVITY SCREENING

Antibodies of Example 15 were screened for cross-reactivity against cyclosporin metabolites using G6PDH conjugate, linking group II. Key selection factors included minimization of cross-reactivity.

TABLE 4

Cross-Reactivity of Antibodies with Metabolites M1, M8, M17, and M21

| SPIKES (ng/ml) | Apparent CsA Concentrations | | |
|---|---|---|---|
|  | 5E10 | 2G4 | 3B5 |
| Control | | | |
| 150 ng/mL CsA | 262.5 | 269.3 | 253.7 |
| Metabolite only | | | |
| 2000 ng/mL M1 | >550 | >500 | >500 |
| 2000 ng/mL M8 | >500 | <50 | >500 |
| 2000 ng/mL M17 | >500 | 103.6 | >500 |
| 2000 ng/mL M21 | 353.1 | 174.5 | 233.3 |
| Metabolite + Parent | | | |
| 2000 ng/mL M1 + 250 ng/mL CsA | >500 | >500 | >500 |
| 2000 ng/mL M8 + 250 ng/mL CsA | >500 | 206.5 | >500 |
| 2000 ng/mL M17 + 250 ng/mL CsA | >500 | 284.3 | >500 |
| 2000 ng/mL M21 + 250 ng/mL CsA | >500 | 323.5 | 348.7 |

TABLE 5

Cross-Reactivity of Antibodies with Metabolite M17

| Clone | 2A3 | 7H4 | 10E6 | 6E5 | 4D7 | 4B10 | 7G10 |
|---|---|---|---|---|---|---|---|
| M17 Conc. (ng/mL) | | | | | | | |
| 0 | <50 | <50 | <50 | <50 | 58 | <50 | <50 |
| 100 | 57 | 59 | <50 | 119 | 136 | 73 | <50 |
| 200 | 86 | 118 | 92 | 175 | 175 | 138 | <50 |
| 350 | 186 | 253 | 140 | 363 | 215 | 238 | 155 |
| 500 | 241 | 304 | 212 | 534 | 286 | 334 | 163 |
| 1000 | 469 | >500 | 415 | >500 | >500 | >500 | 415 |

D. CONCLUSION

Based on the above screening, cyclosporin A conjugated through the linking group of Formula II at the alanine nitrogen atom of cyclosporin A amino acid residue no. 7 to glucose-6-phosphate dehydrogenase was selected as an exemplary enzyme conjugate.

The antibody clone no. 2G4 was selected as an exemplary antibody.

EXAMPLE 17

EMIT ASSAY PERFORMANCE

Details of the EMIT Assay protocol are described in U.S. Pat. No. 3,817,837 (1974). Antibodies prepared by the method of Example 15 using the KLH conjugate of Example 13B were used, and are, for this Example, referred to as anti-CsA monoclonal antibodies. The G6PDH conjugate was prepared by the method of Example 14 using the compound of Example 6B, and is, for this Example, referred to as CsA-G6PDH conjugate. The assay was performed on the COBAS MIRA analyzer.

One hundred microliters of a whole blood sample and 6 calibrators were separately vortexed with 200 μL methanol. The methanol lysed cells, solubilized cyclosporin, and precipitated blood proteins. After a one-minute incubation, the mixture was centrifuged. The supernatant was diluted 1 to 3 with pretreatment diluent. On the analyzer, 36 μL of the resulting pretreated sample were incubated for 75 seconds with 155 μL of the monoclonal anti-CsA antibody reagent, which included substrate and cofactor. Subsequently, 75 μL of the CsA-G6PDH conjugate reagent was added. After a 175 second incubation, enzyme activity, (a function of drug concentration) was monitored by following the production of NADH spectrophotometrically at 340 nm for 100 seconds.

The monoclonal anti-CsA antibody reagent contained monoclonal anti-CsA antibody, nicotinamide adenine dinucleotide, glucose-6-phosphate, sodium chloride, bulking agent, surfactant, and preservatives.

The CsA-G6PDH conjugate reagent contained enzyme conjugate, tris buffer, bulking agents, stabilizers, and preservatives.

The diluent contained tris buffer, surfactant, and preservatives.

Each of the reagents was formulated to be consistent with standard EMIT technology. The reagents were not lyophilized and were therefore liquids. Bulking agents, surfactants and preservatives were selected, which allowed for ease of use and storage of the reagents.

A preferred stabilizer for the CsA-G6PDH conjugate reagent was an antibody, which bound to glucose-6-phosphate dehydrogenase at a site or sites other than enzymatically active sites. Such an antibody was prepared using glucose-6-phosphate dehydrogenase as an immunogen by the standard hybridoma techniques described in Example 15. The anti-G6PDH antibody was used as a stabilizer for the CsA-G6PDH conjugate reagent.

Twenty samples and six calibrators were pretreated and assayed under this protocol in less than two hours.

The assay standard curve range extended to 500 ng/mL. Analytical recovery within the curve range varied from 95 to 104%. Within run precision with trilevel controls ranged from 5.0 to 7.1% CV. Between run precision with the same controls ranged from 4.9 to 7.4% CV.

Cross-reactivity was observed with cyclosporin A metabolite, M1, but not with the other major metabolites, M8, M17, and M21. Fifty-seven potentially coadministered drugs, variations in hematocrit, and high levels of bilirubin or triglycerides did not interfere in the assay.

| ASSAY PARAMETERS ON COBAS MIRA ANALYZER | |
|---|---|
| Assay Temperature | 37° C. |
| Wave length | 340 nm |
| Volume of Pretreated Sample | 36 μL |
| Diluent Volume (water) | 59 μL |
| Antibody Reagent Volume | 155 μL |
| Incubation Time (sample + antibody reagent) | 75 sec |
| Enzyme Reagent Volume | 75 μL |
| Delay Time (sample + antibody and enzyme reagents) | 175 sec |
| Read Time | 100 sec |

Three levels of cyclosporin A were spiked into 10 fresh cyclosporin A-negative whole blood samples. The samples were assayed in duplicate.

| SPIKED CONC. (ng/mL) | 75 | 250 | 400 |
|---|---|---|---|
| N | 10 | 10 | 10 |
| Mean (ng/mL) | 74.3 | 237.1 | 396.7 |
| SD (ng/mL) | 6.2 | 11.8 | 18.0 |
| CV (%) | 8.4 | 5.0 | 4.5 |
| Recovery (%) | 99.0 | 94.8 | 99.2 |

Five levels of cyclosporin A were spiked into two discrete samples of fresh cyclosporin A-negative whole blood. The samples were assayed in duplicate.

| SPIKED CONC. (ng/mL) | 35 | 75 | 150 | 275 | 425 |
|---|---|---|---|---|---|
| N | 2 | 2 | 2 | 2 | 2 |
| Mean (ng/mL) | 41.6 | 77.8 | 151.6 | 277.6 | 420.4 |
| Recovery (%) | 118.8 | 103.7 | 101.1 | 100.9 | 98.9 |

Within-run precision determinations were performed on 20 distinct sample extracts at each of three levels. Between-run precision determinations were performed at each of three levels in a total of 20 runs on two analyzers. Distinct sample extracts were assayed in each run, and quantitations were from concurrent standard curves.

|  | N | Mean (ng/mL) | SD (ng/mL) | CV (%) |
|---|---|---|---|---|
| Within-run | 20 | 82.3 | 5.6 | 6.8 |
|  | 20 | 187.3 | 9.4 | 5.0 |
|  | 20 | 372.2 | 26.4 | 7.1 |
| Between-run | 20 | 91.1 | 6.7 | 7.4 |
|  | 20 | 183.9 | 9.0 | 4.9 |
|  | 20 | 356.6 | 17.5 | 4.9 |

Samples from the American Association of Clinical Chemist/College of American Pathologists (AACC/CAP) Whole Blood Cyclosporin A Survey and the United Kingdom Quality Assessment Scheme (UKQAS) were assayed with the EMIT Cyclosporin A Assay. The results compared favorably with those of HPLC and the CYCLO-Trac SP RIA (INCSTAR).

|  | Mean Cyclosporin A Concentration | | |
|---|---|---|---|
|  | EMIT | HPLC | RIA |
| AACC/CAP Sample ID | | | |
| CS1-A (1989) | 380 | 409 | — |
| CS1-B (1989) | 191 | 188 | 194 |
| CS1-C (1989) | 45 | 44 | 42 |
| CS1-D (1989) | 99 | 96 | 98 |
| CS1-A (1990) | 52 | 59 | 60 |
| UKQAS Sample ID | | | |
| 67A | 135 | 111 | 130 |
| 67B | 195 | 167 | 191 |
| 67C | 449 | 432 | 534 |
| 68A | 159 | 138 | 163 |
| 68B | 169 | 141 | 164 |
| 68C | 160 | 148 | 162 |
| 69A | 134 | 123 | 127 |
| 69B | 200 | 205 | 217 |
| 69C | 161 | 152 | 161 |
| 70A | 152 | 122 | 144 |
| 70B | 249 | 157 | 223 |
| 70C | 98 | 86 | 87 |
| 71A | 122 | 100 | 116 |
| 71B | 154 | 114 | 146 |
| 71C | 314 | 221 | 314 |
| 72A | 247 | 205 | 265 |
| 72B | 119 | 94 | 121 |
| 72C | 124 | 115 | 131 |
| 73A | 273 | 211 | 268 |
| 73B | 190 | 132 | 176 |
| 73C | 97 | 68 | 89 |

Cross-reactivity with the four major cyclosporin A metabolites was evaluated in the presence of 200 ng/mL cyclosporin A. Of these metabolites, only M1 (AM9) showed significant cross-reactivity.

|  | Apparent Cyclosporin A Concentrations | | | |
|---|---|---|---|---|
| Metabolite Level (ng/mL) | M1 (AM9) | M8 (AM19) | M17 (AM1) | M21 (AM4N) |
| 0 | 197 | 197 | 200 | 190 |
| 100 | 231 | 197 | 190 | 173 |
| 200 | 250 | 209 | 203 | 193 |
| 350 | 290 | 207 | 202 | 200 |
| 500 | 312 | 207 | 187 | 194 |
| 1000 | 399 | 226 | 190 | 198 |

The fifty-seven compounds listed below did not cross-react in the assay. They were tested at the following concentrations in the presence of 200 ng/mL cyclosporin A. Substantial cross-reactivity was defined as a 25% or greater elevation in the cyclosporin A concentration.

| Cross-reactant | Testing Level ($\mu$/mL) | Cross-reactant | Testing Level ($\mu$/mL) |
|---|---|---|---|
| acetaminophen | 100 | maprotiline | 100 |
| amikacin | 500 | melphalan | 100 |
| amitriptyline | 500 | methyl prednisone | 100 |
| amphotericin B | 100 | N-acetyl procainamide | 100 |
| ampicillin | 100 | neomycin | 500 |
| azathioprine | 100 | oxytocin | 100 |
| carbamazepine | 500 | phenobarbital | 500 |
| cefotaxime | 100 | phenytoin | 200 |
| cephalosporin | 100 | prednisolone | 10 |
| chloramphenicol | 500 | presnisone | 10 |
| chlordiazepoxide | 100 | primidone | 200 |
| chlorpropamide | 100 | procainamide | 50 |
| cimetidine | 100 | dl-propranolol | 100 |
| cyclophosphamide | 100 | quinidine | 100 |
| diazepam | 100 | rifampicin | 100 |
| digitoxin | 100 | salicyclic acid | 1000 |
| digoxin | 0.1 | spectinomycin | 100 |
| dipyridamole | 100 | streptomycin | 500 |
| disopyramide | 100 | sulfamethazine | 100 |
| encainide | 100 | sulfamethoxazole | 100 |
| erythromycin | 500 | theophylline | 100 |
| ethosuximide | 500 | tobramycin | 500 |
| furosemide | 100 | tocainide | 100 |
| gentamicin | 100 | triamterene | 100 |
| imipramine | 500 | trimethoprim | 100 |
| indomethacin | 100 | valproic acid | 1000 |
| kanamycin | 500 | vancomycin | 100 |
| ketoconazole | 100 | verapamil | 100 |
| lidocaine | 100 | | |

No clinically significant interference was found in the EMIT® Cyclosporin A Assay in the presence of 30 mg/dL bilirubin or 1000 mg/dL triglycerides.

|  | Percent Recovery of Cyclosporin A | |
|---|---|---|
| Cyclosporin A (ng/mL) | 75 | 400 |
| Control | 107.1 | 107.7 |
| Bilirubm (30 mg/dL) | 111.7 | 101.6 |
| Triglycerides (1000 mg/dL) | 102.8 | 102.5 |

Samples with hematocrits ranging from 18% to 66% showed no clinically significant variations in recovery of cyclosporin A at concentrations of 75, 250 and 400 ng/mL.

| Hematocrit (%) | Recovery of Cyclosporin A (%) | | |
|---|---|---|---|
| | 75 ng/mL | 250 ng/mL | 250 ng/mL |
| 18 | 97.3 | 106 | 101 |
| 26 | 95.6 | 108 | 97.0 |
| 38 | 113 | 103 | 97.7 |
| 45 | 107 | 111 | 103 |
| 56 | 104 | 111 | 101 |
| 66 | 105 | 110 | 110 |

EXAMPLE 18

OXYACETIC ACID IMINO EXTENDED ATIOCYCLOSPORIN

Into a stirred solution of cyclosporin A metabolite M-1 (compound (1), scheme I, 6 mg, 4.9×10−3 mmol, obtained from dog urine by the method of Christians, U.; Et. al. *Clinical Chem.* 1988, 34(1), 34–39 using Bio-Beads according to method of Roerig, D. L.; Et. al. *S. Chrmatog.* 1975, 110, 349) in dried methanol (1ml) at −78° C. was passed a stream of oxygen containing ozone (welbach ozone generator, 0.5 mL/min., regulator pressure 6 psi, ozone generator pressure 4 psi, ozone generator running at 80 volts) for 10 minutes (until the solution turned blue), the stream of oxygen containing ozone was discontinued. Argon was passed through the solution for 10–15 min. (until the solution temperature reached −20° C.). Dimethyl sulfide (0.2 ml) was added. The mixture was allowed to warm to room temperature (R.T.) and until most of the methanol was evaporated, the atiocyclosporin carboxaldehyde product (compound (2), Scheme I) was not isolated, purified, or characterized. The reaction mixture containing the ozone cleavage products was redissolved in anhydrous methanol (1 ml) and aminooxyacetic acid (HCl Salt, 12 mg, 0.1 mmol) was added. The mixture was stirred for 2 h at R.T. Dichloromethane (30 ml), a brine/water mixture (1:1, 20 ml), and 2 drops of HCl (in) were added. The dichloromethane layer was separated, dried ($MgSO_4$), and evaporated to dryness to give oxyacetic acid imino extended atiocyclosporin (compound(3), scheme I, 6 mg, 4.7×10−3 mmol, 96%). M.S., m/e 1279.9 (M+H)+. The product was used without purification, but can be further purified by preparative thin layer chromatography (silica gel, ethyl acetate/MeOH/AoCH, 90:10:0.1).

EXAMPLE 19

KEYHOLE LIMPET HEMOCYANIN CONJUGATE OF OXYACETIC ACID IMINO EXTENDED ATIOCYCLOSPORIN

To a stirred solution of the product of Example 18 (compound(3), scheme I, 5 mg, 3.9×10−3 mmol) and N-Hydroxysulfosuccinimide (sulfo-NHS, 11 mg, 1.2×3.9×10−3 mmol) in dried DMF (0.2 ml) was added 1-ethyl-3-(3-dimethylamino propyl) carbodiimide (EDAC, 1.1 mg, 1.6×3.9×10−3 mmol). The mixture was stirred at R.T. under an argon atmosphere for 5 h. Thin layer chromatography (silica gel, ethyl acetate/MeoH/AcOH, 85:15:0.4) was used to monitor the reaction. By this technique, all starting material was consumed. The activated ester product was not isolated, purified, or characterized. To a stirred solution of keyhole limpet hemocyanin (KLH, 64% pure, 17 mg, 2×10−5 mmol) in phosphate buffer (ph≅8.1, 100$_m$M, 2 ml) and DMF (0.2 ml) at 4° C. was added the activated ester product over a 1 h period. The mixture was stirred overnight at 4° C. The mixture was dialyzed against $H_2O$/DMF (80:20, 500 ml) and water. The dialyzed product was lyophilized to give keyhole limpet hemocyanin conjugate of oxyacetic acid imino extended atiocyclosporin (Formula (4), scheme I, 15 mg). This conjugate is also referred to as an M1-KLH conjugate.

EXAMPLE 20

GLUCOSE-G-PHOSPHATE DEHYDROGENASE CONJUGATE OF OXYACETIC ACID IMINO EXTENDED ATIOCYCLOSPRIN

Using the method of Example 14 and the atiocyclosporin Hapten of Example 18, atiocyclosporin conjugated through an oxyacetic acid imino extended linking group to glucose-6-Phosphate dehydrogenase (compound 4), scheme I, wherein, instead of KLH, the conjugation is to G6PDH) was prepared. This conjugate is also referred to as an M1-G6PDH conjugate.

EXAMPLE 21

PREPARATION OF ANTI-M1 MONOCLONAL ANTIBODIES

A. GENERAL METHODS

Using the method of Example 15 and the keyhole limpet hemocyanin conjugate of oxyacetic acid imino extended atiocyclosporin product of Example 19, monoclonal antibodies were prepared.

The glucose-6-phosphate dehydrogenase conjugate of oxyacetic acid imino extended atiocyclosporin product of Example 20 was used for ELISA screening.

B. SELECTION OF ANTI-M1 ANTIBODY

Balb/c mice were immunized. After three immunizations (100 ug/injection/mouse, monthly) mice were bled from the tail vein and serum antibody titers were determined. By Forward ELISA protocol, serial dilutions of sera were screened against both CsA-G6PDH and M1-G6PDH. The initial titers were about 3 times higher against M1-G6PDH than CsA-G6PDH. The titers were 1:30,000 when screened against M1-G6PDH while only 1:10,000 titer against CsA-G6PDH.

Four fusions were performed. At time of fusion, spleens were slightly enlarged indicating an elevated immune response. The size of spleen ranged from 0.25 to 0.5 mL determined by displacement.

Primary screens were performed on replicate plates, coated with rabbit α-mouse IgG+IgA+IgM chain (Zymed #61-6400SY) by Reverse ELISA. The primary screen response varied from 3 to 36 ELISA-positive wells per fusion.

Secondary screens were performed by EMIT. Antibodies were tested for ability to inhibit CsA-G6PDH. Antibodies were selected which, in presence of anti-CsA antibodies, demonstrated reversal of inhibition in the presence of CsA but did not demonstrate reversal of inhibition in the presence of M1; and inhibited M1-G6PDH but did not substantially bind CsA or inhibit CsA-G6PDH. One antibody (clone 2B10) was selected as the anti-M1 monoclonal antibody.

C. PREPARATION AND PURIFICATION OF ANTI-M1 ANTIBODY

Cells capable of producing the anti-M1 monoclonal antibody were grown up in spinner flasks at 37° C. and 7% $CO_2$. Cultures were maintained by feeding with fresh media and splitting cultures to additional or larger vessels. Cell counts and viability determinations by Trypan Blue were performed routinely to monitor cell growth. Paragon gel electrophoresis on 5× to 10× concentrated spent media were also routinely performed to monitor antibody production. After 10 days, the cultures were centrifuged in a Beckman RC2B centrifuge at 5000 rpm for 15 minutes and at 4° C. to remove the cells from the antibody.

The antibody in 15 L of culture fluid was concentrated 5-fold and dialyzed into 10 mM MES buffer.

The antibody was purified by column chromatography on Bakerbond ABx (J. T. Baker Inc #7269-00). A column, 50 cm high with a 2.6 cm diameter, was packed with about 100 grams of ABx equilibrated in 10 mM MES buffer. Antibody was loaded at 5 mL/min and then eluted with a 1 L gradient from 10 mM MES pH 5.6 to 200 mM NaCl/100 mM Tris pH 7.4. Samples were collected from the column in 10 mL fractions and the absorbance monitored at 280 nm for protein content. Antibody containing fractions were pooled.

EXAMPLE 22

EMIT ASSAY PERFORMANCE WITH ANTI-M1 ANTIBODY

The assay of Example 17 was performed using a monoclonal anti-CsA antibody reagent, which contained, in addition to the contents specified in Example A, the Anti-M1 antibody of Example 21.

Cross-reactivity with the four major cyclosporin A metabolites was evaluated in the presence of 200 ng/mL cyclosporin A. No clinically significant cross-reactivity (clinically significant cross-reactivity is cross-reactivity, which increased CsA quantitation by $\geq 20\%$) was observed with metabolites M1, M8, M17, or M21.

Other aspects of the assay performance were substantially unaffected.

| APPARENT CYCLOSPORINE CONCENTRATIONS | | | | |
|---|---|---|---|---|
| Metabolite Level (ng/mL) | M1 (AM9) | M8 (AM19) | M17 (AM1) | M21 (AM4N) |
| 0 | 200 | 200 | 200 | 200 |
| 100 | 203 | 205 | 210 | 200 |
| 200 | 208 | 198 | 199 | 214 |
| 350 | 215 | 208 | 201 | 206 |
| 500 | 224 | 215 | 194 | 201 |
| 1000 | 249 | 223 | 201 | 198 |

Although the foregoing invention has been described in some detail by way of illustration, it will be obvious that certain changes and modifications may be practiced within the scope of the appended claims. Particularly, minor changes in the structure of the linking groups of the compounds of the present invention can be made. Such modifications, which do not significantly change the properties of the compounds or antibodies of the present invention, are considered obvious.

What is claimed is:

1. An assay for the presence of cyclosporin in a sample suspected of containing cyclosporin, wherein the assay comprises:

(A) combining in an aqueous medium:
1) said sample suspected of containing cyclosporin,
2) a cyclosporin-label conjugate comprising cyclosporin conjugated at an alanine nitrogen atom of amino acid residue 7 or 8 to a label, and
3) antibodies capable of binding to said cyclosporin-label conjugate, wherein said antibodies have been raised against a cyclosporin-immunogenic carrier conjugate comprising cyclosporin conjugated to an immunogenic carrier, (B) determining the presence of a detectable complex; and (C) correlating said detectable complex with the presence of cyclosporin in said sample;

wherein said cyclosporin is conjugated to said label and said immunogenic carrier through a first and a second linking group, respectively;

wherein said linking groups are independently selected from the group consisting of (I) a hydroxyalkane chain of the formula $-(CH_2)_nO-$, where n is an integer of about 1 to 6;

(II) a carboxyl benzyl group of the formula:

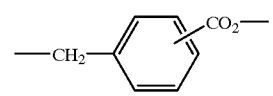

wherein an alanine nitrogen atom of cyclosporin is conjugated to the benzylic carbon atom in the carboxyl benzyl group; and (III) a moiety of the formula:

(i)

(ii)

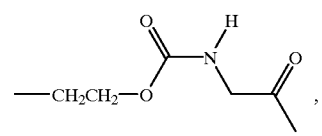

(iii)

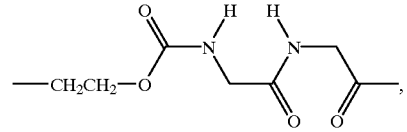

(iv)

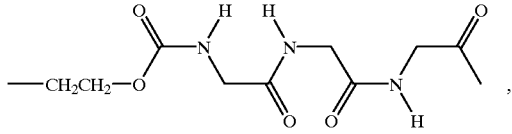

(v)

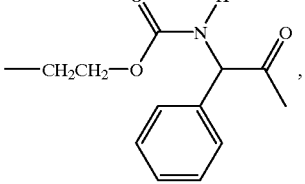

(vi)

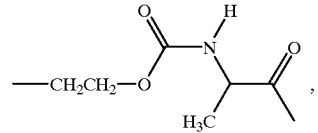

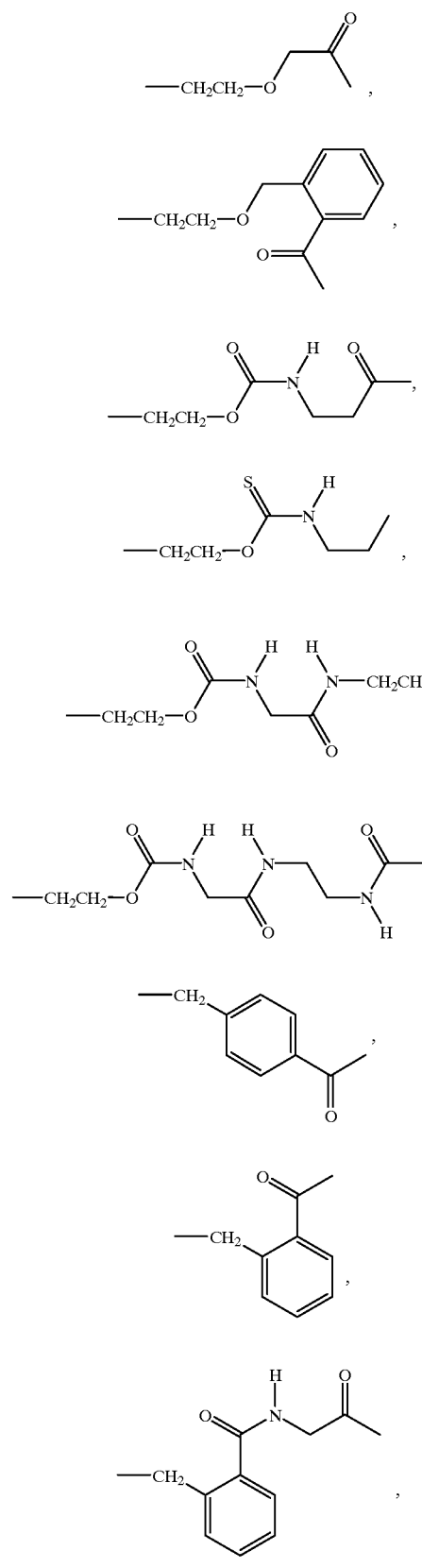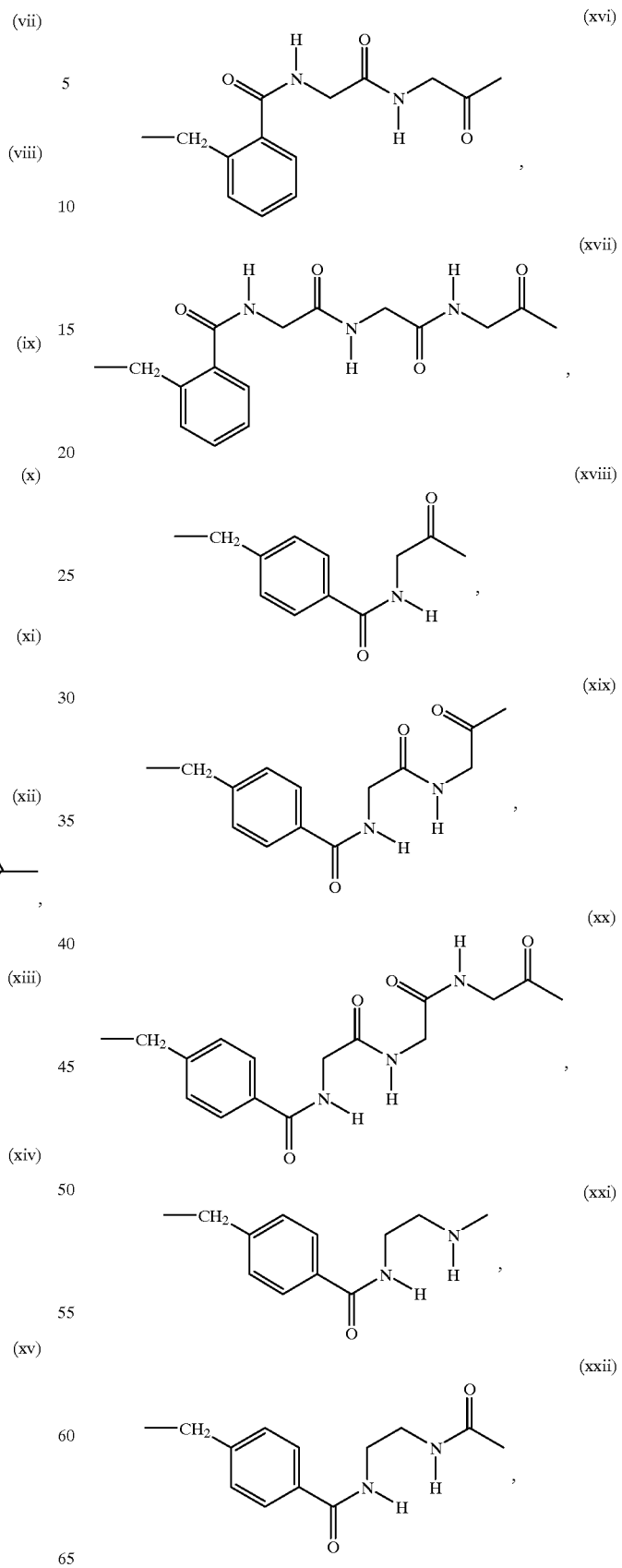

-continued

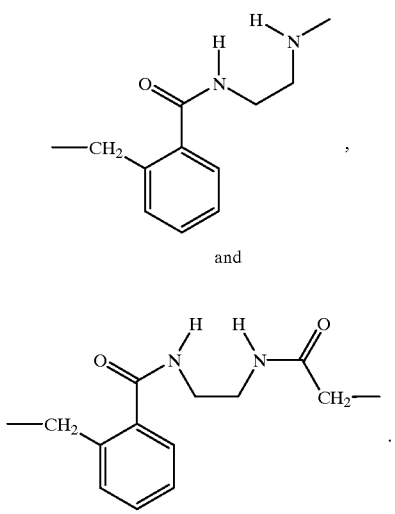

(xxiii)

and (xxiv)

2. The assay of claim 1, which further comprises determining the amount of cyclosporin in said sample.

3. The assay of claim 1, wherein said label is an enzyme, and said assay comprises measuring the activity of said enzyme.

4. The assay of claim 1, wherein said label is a dehydrogenase, and said assay comprises measuring the activity of said dehydrogenase.

5. The assay of claim 1, wherein said label is glucose-6-phosphate dehydrogenase, and said assay comprises measuring the activity of said glucose-6-phosphate dehydrogenase.

6. The assay of claim 1, which comprises the step of measuring the amount of said cyclosporin-label conjugate bound to said antibodies.

7. The assay of claim 1, which comprises the step of pretreating said sample with an alcohol.

8. The assay of claim 7, wherein said alcohol is methanol.

9. The assay of claim 1, wherein said cyclosporin is cyclosporin A.

10. The assay of claim 1, wherein n in the hydroxy-alkane group is about 2 to 4.

11. The assay of claim 1, wherein n in the hydroxy-alkane group is 2.

12. The assay of claim 11, wherein amino acid residue no. 1 of cyclosporin is substantially unmodified.

13. The assay of claim 1, wherein one or both of amino acid residues no. 7 and no. 8 of cyclosporin is d-alanine, 1-alanine, or a mixture thereof.

14. The assay of claim 1, wherein the antibodies are capable of specifically recognizing a cyclosporin containing an unmodified 9 carbon atom at position 1.

15. The assay of claim 1, wherein said cyclosporin is cyclosporin A conjugated at the alanine nitrogen atom of amino acid residue no. 7 through the linking group of formula (ii) to glucose-6-phosphate dehydrogenase.

16. The assay of claim 1, wherein said cyclosporin is cyclosporin A conjugated at the alanine nitrogen atom of amino acid residues no. 7 and no. 8 through the linking group of formula (xix) to keyhole limpet hemocyamin.

17. The assay of claim 1, wherein the antibody inhibits activity of glucose-6-phosphate dehydrogenase.

18. The assay of claim 1, wherein the presence of cyclosporin is determined by chemiluminescence.

19. The assay of claim 18, wherein chemiluminescence is obtained from a dioxetane.

20. The assay of claim 1, wherein the hydroxyalkane linking group is extended at the oxygen by about 1 to about 3 carboxamide groups linked together by alkylene chains.

21. The assay of claim 20, wherein the alanine nitrogen is part of cyclosporin amino acid residue 7.

22. The assay of claim 1, wherein the carboxyl group in the carboxyl benzyl group is ortho or para to the benzylic carbon.

23. The assay of claim 22, wherein the carboxyl benzyl group is extended at an oxygen atom of the carboxyl group by from about 1 to about 3 carboxamide groups linked together by alkylene chains.

24. The assay of claim 1, which comprises including in said aqueous medium a second antibody capable of binding to metabolites of cyclosporin.

25. The assay of claim 24, wherein said label is selected from the group consisting of enzymes, enzyme fragments, enzyme substrates, enzyme inhibitors, coenzymes, fluorophores, dyes, particles, solid supports, liposomes, chemiluminescers, luminescers, radioactive isotypes, catalysts, ligands, hastens, and sensitizers.

26. The assay of claim 24, wherein said label is glucose-6-phosphate dehydrogenase.

27. The assay of claim 24, wherein said label is a fluorophore.

28. The assay of claim 24, wherein said metabolite is cyclosporin metabolite M1.

29. The assay of claim 1, further comprising including in said aqueous medium a second antibody that binds to the cyclosporin metabolite M1 and has been raised against a composition of the formula:

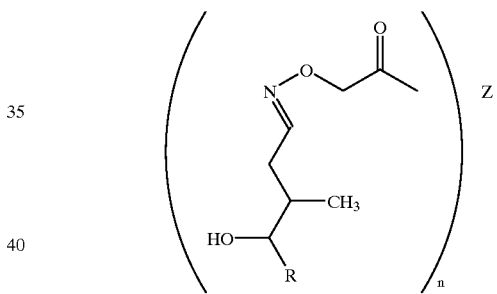

where R is of the formula:

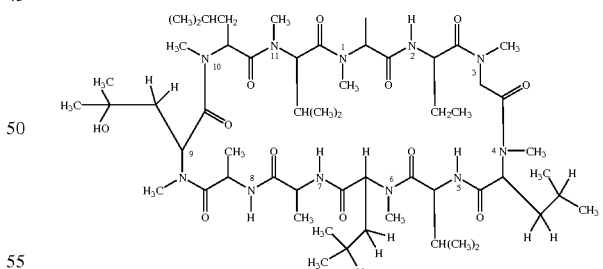

Z is an immunogenic carrier, and n is a number from 1 up to the molecular weight of Z divided by 5000.

30. The assay of claim 29, wherein the immunogenic carrier is a protein, a polysaccharide, a lipoprotein, or a glycoprotein.

31. The assay of claim 1, wherein said linking group is said carboxyl benzyl group.

32. The assay of claim 31, wherein said carboxyl group is para to the benzylic carbon.

33. An assay for the presence of cyclosporin in a sample suspected of containing cyclosporin, wherein the assay comprises:
  (A) combining in an aqueous medium;
    1) said sample suspected of containing cyclosporin,
    2) a cyclosporin-label conjugate comprising cyclosporin conjugated at one of its alanine nitrogen atoms to a label, and
    3) antibodies capable of binding to said cyclosporin-label conjugate, wherein said antibodies have been raised against a cyclosporin-immunogenic carrier conjugate comprising cyclosporin conjugated at one of its alanine nitrogen atoms to an immunogenic carrier,
  (B) determining the presence of a detectable complex; and
  (C) correlating said detectable complex with the presence of cyclosporin in said sample;
    wherein said cyclosporin is conjugated to said label through a first linking group;
    and further wherein one or both of amino acid residues 7 and 8 of said cyclosporin are d-alanine, 1-alanine, or a mixture thereof, and said conjugation is at amino acid residue 7 or 8 or at amino acid residues 7 and 8.

34. The assay of claim 33, wherein said linking groups are independently selected from the group consisting of moieties of less than about 50 atoms other than hydrogen having a chain of not more than about 35 atoms in length.

35. The assay of claim 34, wherein said linking groups have chains less than about 20 atoms other than hydrogen.

36. The assay of claim 35, wherein said chain comprises about 25 atoms in length.

37. The assay of claim 36, wherein said chain comprises about 15 atoms in length.

38. The assay of claim 33, wherein said conjugation to cyclosporin is through said first linking group at amino acid residue 7 or amino acid residues 7 and 8.

39. The assay of claim 33, wherein said cyclosporin is conjugated to said immunogenic carrier through a second linking group.

40. The assay of claim 39, wherein said conjugation to cyclosporin is through said first and said second linking groups at amino acid residue 7 or amino acid residues 7 and 8.

41. An assay for the presence of cyclosporin in a sample suspected of containing cyclosporin, wherein the assay comprises:
  (A) combining in an aqueous medium:
    1) said sample suspected of containing cyclosporin,
    2) a cyclosporin-label conjugate comprising cyclosporin conjugated at one of its alanine nitrogen atoms to a label, and
    3) antibodies capable of binding to said cyclosporin-label conjugate, wherein said antibodies have been raised against a cyclosporin-immunogenic carrier conjugate comprising cyclosporin conjugated at one of its alanine nitrogen atoms to an immunogenic carrier,
  (B) determining the presence of a detectable complex; and
  (C) correlating said detectable complex with the presence of cyclosporin in said sample;
    wherein both said label and said immunogenic carrier are conjugated to cyclosporin without linking groups;
    and further wherein one or both of amino acid residues 7 and 8 of said cyclosporin are d-alanine, 1-alanine, or a mixture thereof, and said conjugation is at amino acid residue 8 or at amino acid residues 7 and 8.

42. The assay of claim 41, wherein said linking groups are independently selected from the group consisting of moieties of less than about 50 atoms other than hydrogen having a chain of not more than about 35 atoms in length.

43. The assay of claim 42, wherein said linking groups have chains less than about 20 atoms other than hydrogen.

44. The assay of claim 43, wherein said chain comprises about 25 atoms in length.

45. The assay of claim 43, wherein said chain comprises about 15 atoms in length.

46. The assay of claim 41, wherein said conjugation to cyclosporin is without linking groups at amino acid residue 8.

47. The assay of claim 41, wherein said conjugation to cyclosporin is without linking groups at amino acid residues 7 and 8.

48. A method for measuring the amount of cyclosporin in a sample suspected of containing cyclosporin, which comprises the steps of:
  (A) combining in an aqueous medium:
    (1) said sample suspected of containing cyclosporin,
    (2) a cyclosporin label conjugate comprising cyclosporin conjugated at an alanine nitrogen atom of amino acid residue 7 or 8 to a label, and
    (3) antibodies capable of binding to said cyclosporin label conjugate;
  (B) determining the presence of a detectable complex; and
  (C) correlating said detectable complex with the presence of cyclosporin in said sample.

49. A method for measuring the amount of cyclosporin in a sample suspected of containing cyclosporin, which comprises the steps of:
  (A) combining in an aqueous medium:
    (1) said sample suspected of containing cyclosporin,
    (2) a cyclosporin enzyme conjugate comprising cyclosporin conjugated at an alanine nitrogen atom of amino acid residue 7 or 8 to an enzyme,
    (3) antibodies capable of binding to said cyclosporin enzyme conjugate, and
    (4) substrates for said enzyme;
  (B) determining the presence of a detectable complex by measuring the activity of said enzyme; and
  (C) correlating said detectable complex with the presence of cyclosporin in said sample.

50. A method for measuring the amount of cyclosporin in a sample suspected of containing cyclosporin, which comprises the steps of;
  (A) combining in an aqueous medium:
    (1) said sample suspected of containing cyclosporin,
    (2) a cyclosporin glucose-6-phosphate dehydrogenase conjugate comprising cyclosporin conjugated at an alanine nitrogen atom of amino acid residue 7 or 8 to glucose-6-phosphate dehydrogenase,
    (3) antibodies capable of binding to said cyclosporin glucose-6-phosphate dehydrogenase conjugate, and
    (4) substrates of glucose-6-phosphate dehydrogenase;
  (B) determining the presence of a detectable complex by measuring glucose-6-phosphate dehydrogenase activity; and
  (C) correlating said detectable complex with the presence of cyclosporin in said sample.

51. A method for measuring the amount of cyclosporin in a sample suspected of containing cyclosporin comprising the steps of:
  (A) combining in an aqueous medium;
    (1) said sample suspected of containing cyclosporin,
    (2) a cyclosporin conjugate comprising cyclosporin conjugated to a label at the alanine nitrogen atom of amino acid 7 or 8, (3) a first antibody capable of binding to cyclosporin and to said cyclosporin conjugate, and (4) a second antibody capable of binding to metabolites of cyclosporin;

(B) determining the presence of a detectable complex by determining activity of said label; and (C) correlating said detectable complex with the presence of cyclosporin in said sample.

52. A method for detecting cyclosporin A in a sample suspected of containing cyclosporin A, comprising the steps of:

(A) combining in an aqueous medium:

(1) said sample suspected of containing cyclosporin A, (2) a cyclosporin A conjugate comprising cyclosporin A conjugated to glucose-6-phosphate dehydrogenase at the alanine nitrogen atom of amino acid 7 or 8, (3) a first antibody capable of binding to cyclosporin A and to said cyclosporin A conjugate, (4) a second antibody capable of binding to cyclospori.n metabolite M1, and (5) substrates of glucose-6-phosphate dehydrogenase;

(B) determining the presence of a detectable complex by measuring the glucose-6-phosphate dehydrogenase activity; and (C) correlating said detectable complex with the presence of cyclosporin A in said sample.

53. An assay for the determination of cyclosporin in a sample suspected of containing cyclosporin, wherein the assay comprises the steps of:

(1) contacting the sample with antibodies that recognize cyclosporin, wherein said antibodies are prepared in response to a compound of the formula:

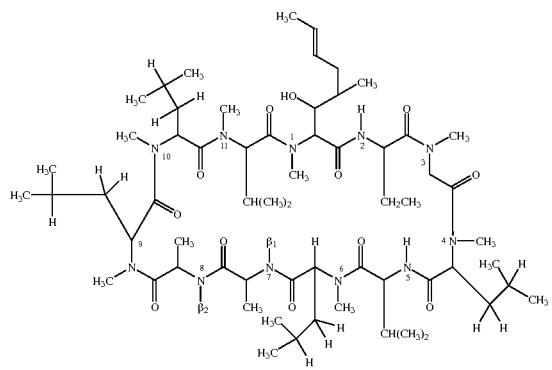

wherein one member of the group $\beta_1$ and $\beta_2$ is hydrogen and the other member is an immunogenic carrier; and (2) detecting the binding of said antibodies to said cyclosporin.

54. An assay for the determination of cyclosporin in a sample suspected of containing cyclosporin, wherein the assay comprises the steps of:

(1) contacting the sample with antibodies that recognize cyclosporin and a compound of the formula:

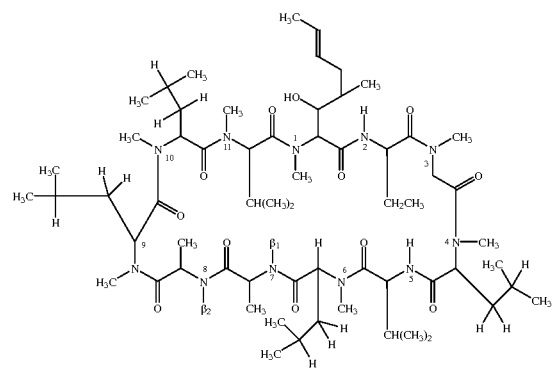

wherein one member of the group $\beta_1$ and $\beta_2$ is hydrogen and the other member is a label; and (2) detecting immune complexes of said compound and said antibodies.

55. A kit for conducting an assay for the determination of cyclosporin, said kit comprising:

(A) antibodies as defined in claim 1, and (B) a cyclosporin-label conjugate as defined in claim 1.

56. A kit for conducting an assay for the determination of cyclosporin, said kit comprising antibodies that recognize a compound of the formula:

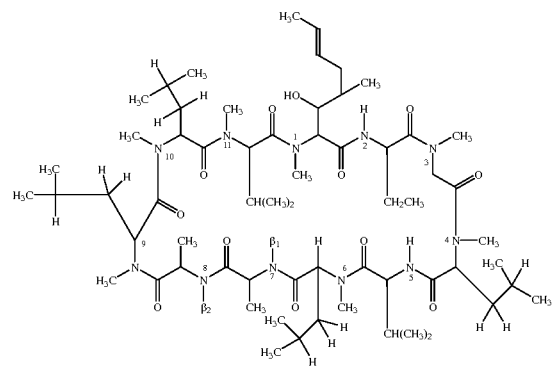

wherein one member of the group $\beta_1$ and $\beta_2$ is hydrogen and the other member is an immunogenic carrier.

57. A kit for conducting an assay for the determination of cyclosporin, said kit comprising antibodies that recognize cyclosporin and a compound of the formula:

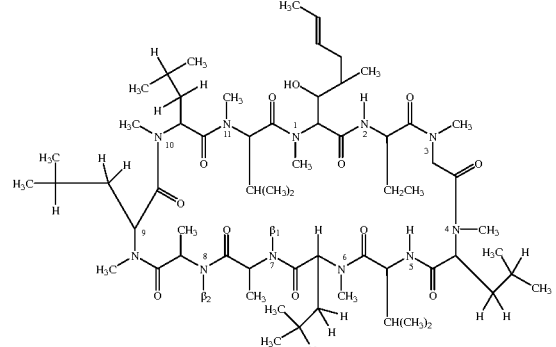

wherein one member of the group $\beta_1$ and $\beta_2$ is hydrogen and the other member is a label.

* * * * *